United States Patent
Pearce et al.

(10) Patent No.: US 9,982,312 B2
(45) Date of Patent: May 29, 2018

(54) MICROBIAL ASSAY

(75) Inventors: David Pearce, Bristol (GB); Mark Enright, Bedfordshire (GB)

(73) Assignee: Atlas Genetics Limited, Bristol (GB)

( * ) Notice: Subject to any disclaimer, the term of this patent is extended or adjusted under 35 U.S.C. 154(b) by 618 days.

(21) Appl. No.: 13/516,600

(22) PCT Filed: Dec. 17, 2010

(86) PCT No.: PCT/GB2010/052130
§ 371 (c)(1),
(2), (4) Date: Jan. 29, 2013

(87) PCT Pub. No.: WO2011/073675
PCT Pub. Date: Jun. 23, 2011

(65) Prior Publication Data
US 2013/0209998 A1    Aug. 15, 2013

(30) Foreign Application Priority Data
Dec. 17, 2009   (GB) .................................. 0922097.1

(51) Int. Cl.
*C12Q 1/68*   (2018.01)
(52) U.S. Cl.
CPC ......... *C12Q 1/689* (2013.01); *C12Q 2600/16* (2013.01)
(58) Field of Classification Search
CPC .................................................... C12Q 1/689
See application file for complete search history.

(56) References Cited

U.S. PATENT DOCUMENTS

| 5,837,469 A | 11/1998 | Harris |
| 7,041,490 B1 * | 5/2006 | Griffais et al. ............ 435/252.3 |
| 7,270,981 B2 | 9/2007 | Armes et al. |

FOREIGN PATENT DOCUMENTS

| EP | 0915172 A2 | 5/1999 |
| JP | 11-196883 | 7/1999 |
| WO | WO 9947706 A1 * | 9/1999 |
| WO | WO-03074731 A2 | 9/2003 |
| WO | WO2006038752 A1 | 4/2006 |
| WO | WO2007020656 A1 | 2/2007 |
| WO | WO-2007020656 A1 | 2/2007 |
| WO | WO 2008134867 A1 * | 11/2008 ........... C12Q 1/6869 |
| WO | WO2009066818 A1 | 5/2009 |

OTHER PUBLICATIONS

Bell, K.S. et al. Proceedings of the National Academy of Sciences USA 101(30):11105 (Jul. 27, 2004).*
Kerman, K. et al. Measurement and Science Technology 15:R1 (2004).*

(Continued)

*Primary Examiner* — Diana B Johannsen
(74) *Attorney, Agent, or Firm* — Mintz Levin Cohn Ferris Glovsky and Popeo, P.C.

(57) ABSTRACT

A method of detecting genetic material deriving from *Chlamydia trachomatis* comprising detection of a specified nucleic acid sequence, optionally using specific primers and probes and optionally in combination with the detection of genetic material deriving from *Pectobacterium atrosepticum* as an internal control; and related products and kits.

19 Claims, 9 Drawing Sheets

(56) References Cited

OTHER PUBLICATIONS

Figure 4:
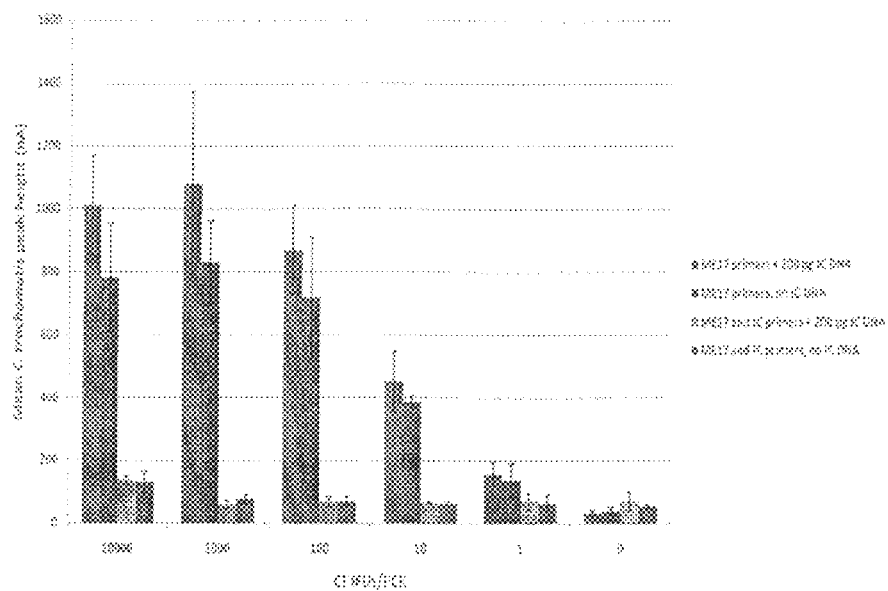

Seth-Smith Helena MB et al: "Co-evolution of Genomes and Plasmids within Chlamydia Trachomatis and the Emergence in Sweden of a New Variant Strain," BMC Genomics, Biomed Central, London, GB, May 21, 2009, p. 239.
Carlson John H. et al: "Comparative Genomic Analysis of Chlamydia Trachomatis Oculotropic and Genitotropic Strains," Infection and Immunity, American Society for Microbiology, Washington, US, vol. 73, No. 10, Oct. 1, 2005, pp. 6407-6418.
Sachse K. et al: "Recent Developments in the Laboratory Diagnosis of Chlamydial Infections," Veterinary Microbiology, Elsevier BV, NL, vol. 135, No. 1-2, Mar. 16, 2009, pp. 2-21.
International Search Report Application No. PCT/GB2010/052130, Dated Jul. 27, 2011.
Gunnhild W. Takle et al., Evaluation of reference geners for real-time RT-PCR expression studies in the plant pathogen Pectobacterium atrosepticum, BMC Plant Biology, Sep. 2007, pp. 2-10.
Torvald Ripa et al., A Chlamydia trachomatis Strain With a 377-bp Deletion in the Cryptic Plasmid Causing False-Negative Nucleic Acid Amplification Tests, Sexually Transmitted Diseases, May 2007, vol. 34, No. 5, pp. 255-256.
F. Fallah et al., Detection of Chlamydia trachomatis from Urine Specimens by PCR in Women with Cervicitis, Iranian J. Publ. Heath, 2005, vol. 34, No. 2, pp. 20-26.
Hamid Jalal et al., Development and Validation of a Rotor-Gene Real-Time PCR Assay for Detection, Identification, and Quantification of Chlamydia trachomatis in a Single Reaction, Journal of Clinical Microbiology, Jan. 2006, pp. 206-213.
Aittamaaet al. Distinguishing bacterial pathogens of potato using a genome-wide microarray approach. Mol Plant Pathol. Sep. 2008;9(5):705-17.
Park et al. PCR-based sensitive and specific detection of Pectobacterium atrosepticum using primers based on Rhs family gene sequences. Plant Pathology 2006; 55: 625-629.
Compton J. Nucleic acid sequence-based amplification. Nature. Mar. 7, 1991 7;350(6313):91-2.
Hoff M. DNA amplification and detection made simple (relatively). PLoS Biol. Jul. 2006;4(7):e222.
Kutyavin et al., 3'-minor groove binder-DNA probes increase sequence specificity at PCR extension temperatures. Nucleic Acids Res. Jan. 15, 2000;28(2):655-61.
Notomi et al., Loop-mediated isothermal amplification of DNA. Nucleic Acids Res. Jun. 15, 2000;28(12):E63.
Vincent et al., Helicase-dependent isothermal DNA amplification. EMBO Rep. Aug. 2004;5(8):795-800.
Walker et al., Strand displacement amplification—an isothermal, in vitro DNA amplification technique. Nucleic Acids Res. Apr. 11, 1992;20(7):1691-6.
Wiedmann et al., Ligase chain reaction (LCR)—overview and applications. PCR Methods Appl. Feb. 1994;3(4):S51-64.
Wroblewski et al., Comparison of transcription-mediated amplification and PCR assay results for various genital specimen types for detection of Mycoplasma genitalium. J Clin Microbiol. Sep. 2006;44(9):3306-12.

\* cited by examiner

Figure 1a - Plasmid amplicon 3 Limit of Detection (LOD)
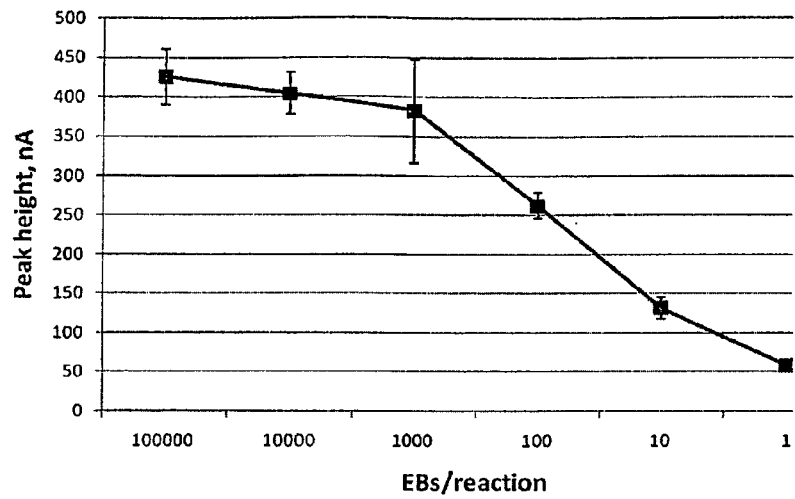
Figure 1b - Plasmid amplicon 5 LOD
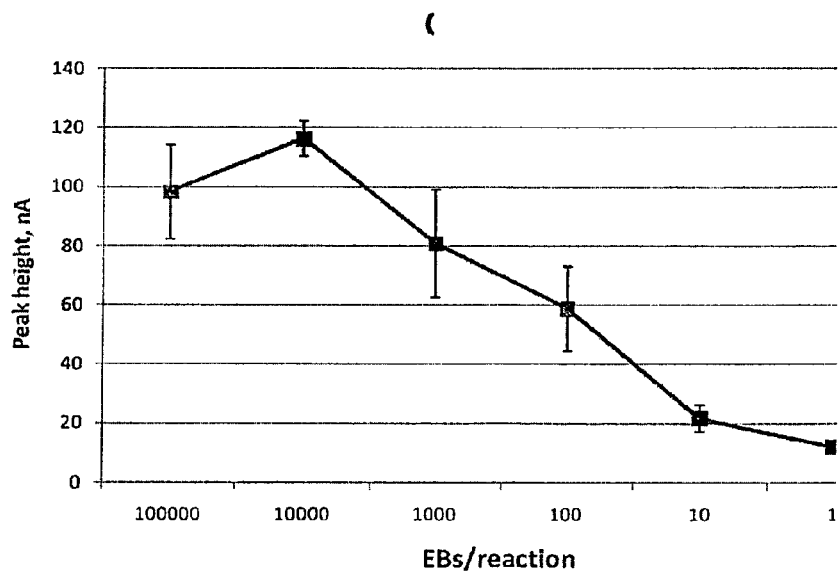

Figure 1c - plasmid amplicon 7 LOD
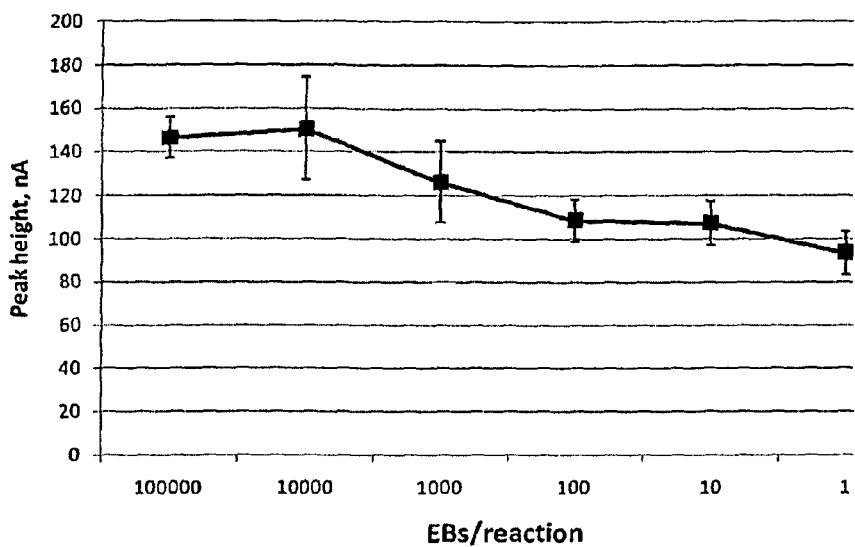
Figure 2a - chromosomal amplicon 9 Limit of Detection (LOD)
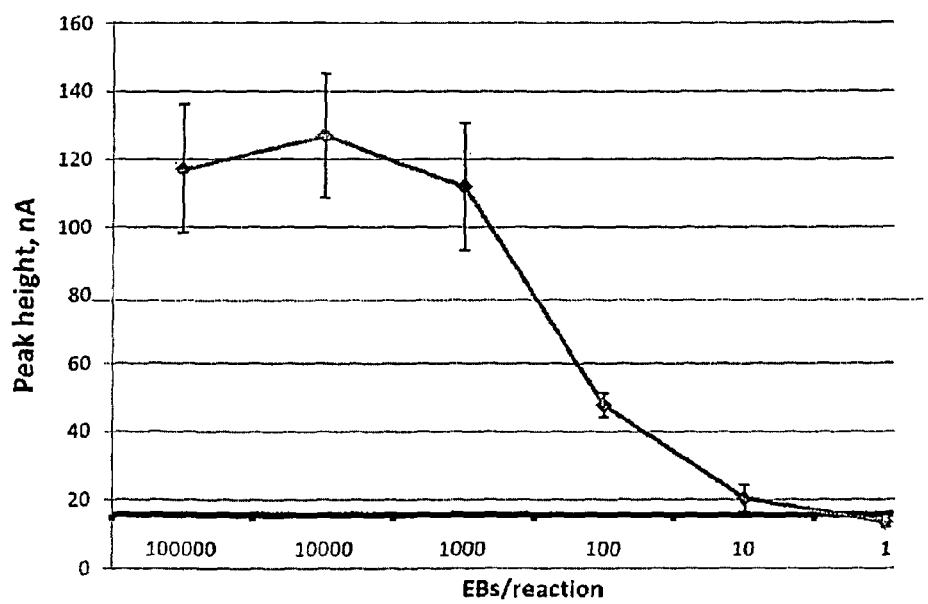

Figure 2b - Chromosomal amplicon 17 LOD
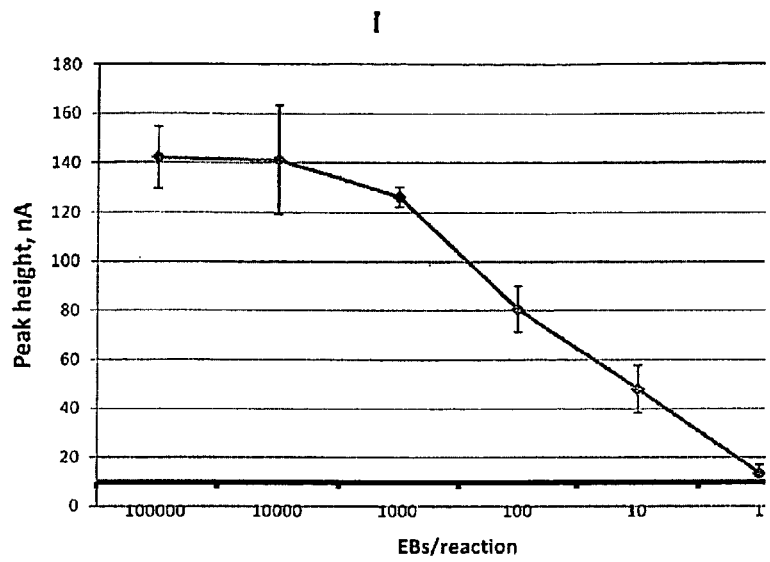
Figure 2c - Chromosomal amplicon 18 LOD
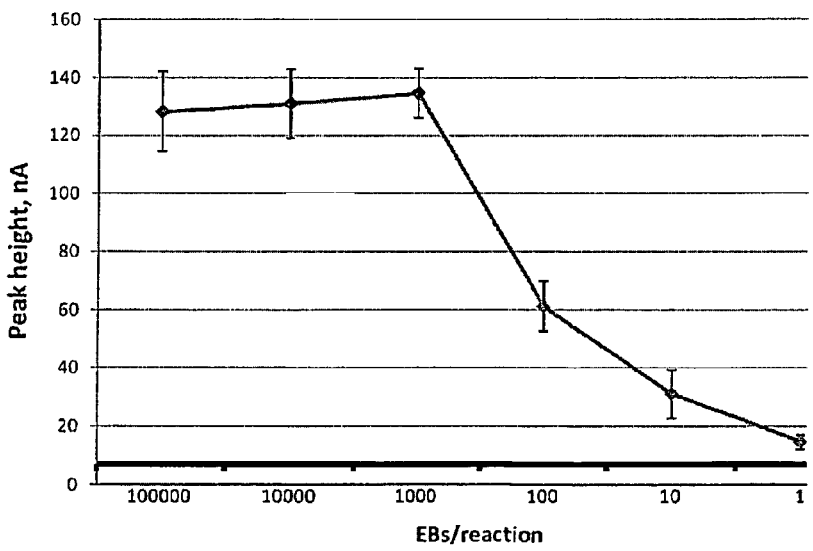

Figure 2d – Chromosomal amplicon 17 LOD at using a final concentration of 5.0 mM MgCl₂
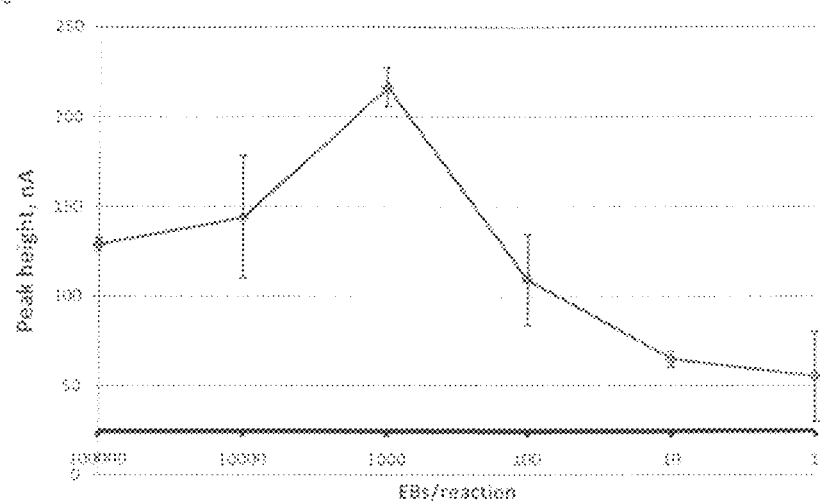
Figure 3 – Chromosomal amplicon 17 LoD using a final concentration of 5.0 mM MgCl₂
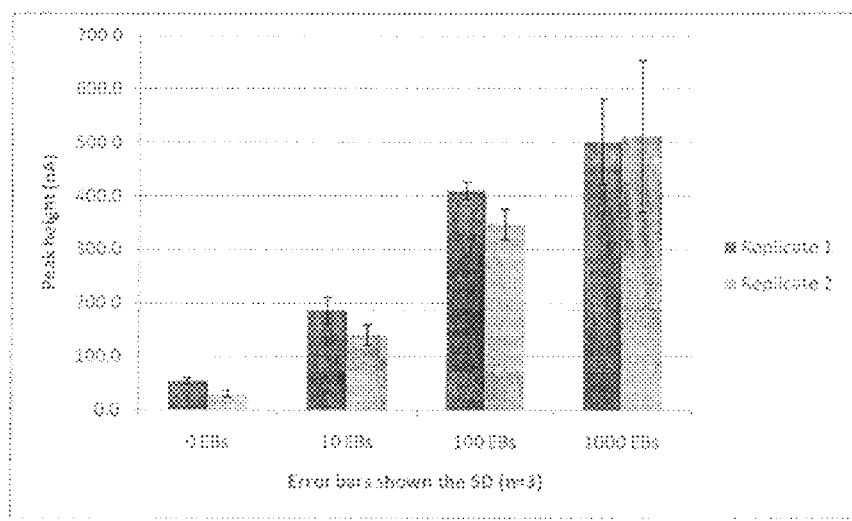

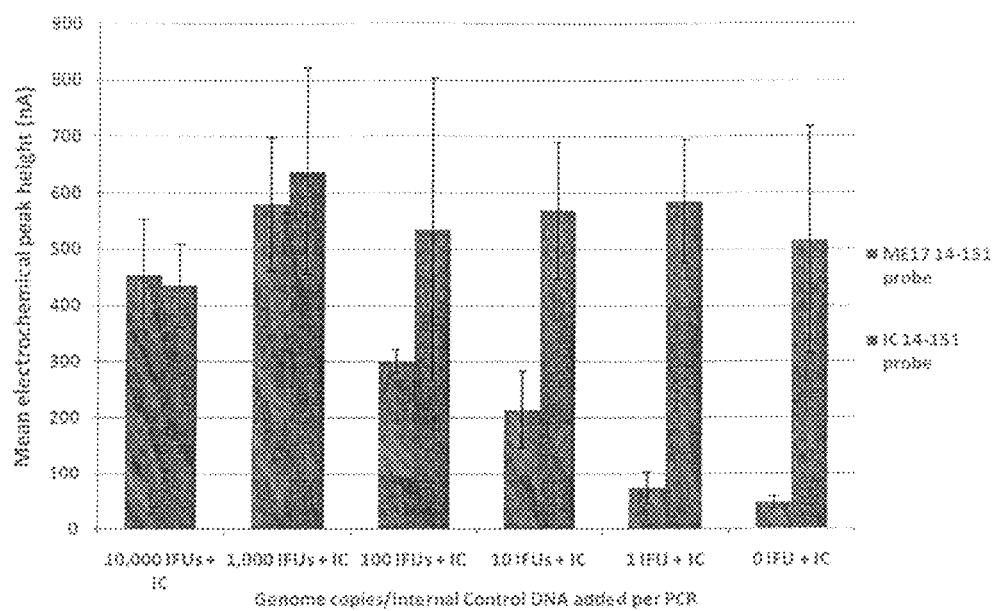
Figure 8 - Electrochemical detections of samples amplified in duplex using the new *C. trachomatis* and Internal Control primer sets. Two hundred picograms of Internal Control DNA was added in all cases. Error bars show the SD (n=3).

MICROBIAL ASSAY

This application is the United States national phase filing of the corresponding international application number PCT/GB2010/052130, filed on Dec. 17, 2010, which claims priority to and benefit of GB Application No. 0922097.1, filed Dec. 17, 2009, which applications are hereby incorporated by reference in their entirety.

FIELD OF INVENTION

The present invention relates to assay products, uses and methods, especially those involving the Polymerase Chain Reaction (PCR). More specifically it relates to assays for *Chlamydia trachomatis* and to improved controls for PCR.

BACKGROUND TO INVENTION

*Chlamydia trachomatis* is an obligate intracellular human pathogen. *Chlamydia* infection is a common sexually-transmitted disease and the bacterium can cause numerous disease states in both men and women. Clinical symptoms include urethritis, proctitis, trachoma, infertility, prostatitis, epididymitis, cervicitis, pelvic inflammatory disease (PID) and ectopic pregnancy. It is also a neonatal pathogen where it can cause infection of the eyes and lungs.

Infection with *Chlamydia trachomatis* is one of the most common sexually transmitted diseases worldwide. It is estimated that 2-3 million individuals in the United States are infected with *Chlamydia*. In the United Kingdom, it has been estimated that one in ten sexually active young people under 25 are infected with *Chlamydia*.

*Chlamydia trachomatis* infection can be successfully treated by antibiotics, for example, tetracyclines such as doxycycline or acrolides such as azithromycin. In order to ensure that appropriate treatment is given in timely fashion, there is a need to accurately diagnose infection by *Chlamydia trachomatis*. In some countries such as the UK, a national programme of *Chlamydia* screening has been launched.

The infectious unit of *Chlamydia trachomatis* is the elementary body (EB). The EB functions as a "spore-like" body whose purpose is to permit Chlamydial survival in a non-supportive environment outside of the host cell. The EB is thought to be metabolically inert until it attaches to and is endocytosed by a susceptible host cell. Detection of *Chlamydia trachomatis* is possible by nucleic acid amplification methods, for example, Polymerase Chain Reaction (PCR) based methods. PCR has the potential to amplify nucleic acid from both infected cells and EBs. *Chlamydia trachomatis* contains genetic material in both its chromosome, which is present as a single copy, and in its plasmid which is present in, 6 to 10 copies per EB. Historically, the plasmid has been used as a preferred target for nucleic acid amplification tests due to its multiple copies per EB and the assumed greater sensitivity obtainable by detecting a plasmid-based target. However, suitability of the plasmid nucleic acid amplification test detection systems has been called into question following the discovery of the Swedish variant of *Chlamydia trachomatis*. The Swedish variant contains a 377 base pair deletion in the plasmid and therefore detection systems targeted at the deleted region will give a false negative result when confronted with Swedish variant *Chlamydia trachomatis*.

The present invention is based on the realisation that an assay detecting sequence present in the *Chlamydia trachomatis* chromosome is potentially more stable because the chromosomal genes are in general less mutable and because in certain circumstances it may be possible for the plasmid to be lost entirely. Targeting a gene present in the chromosome might be expected to be disadvantageous because chromosomal targets are only present as a single copy per cell. However, the inventors of the present invention were surprised to discover that chromosomal targets are able to provide limits of detection (LOD) comparable to plasmid targets.

Nucleic Acid Amplification Tests (NAATs)

A number of nucleic acid amplification test (NAAT) methods suitable for use with the invention are available. They include the well-known PCR, the ligase chain reaction (LCR), strand displacement amplification (SDA), recombinase-polymerase amplification (RPA), transcription mediated amplification, nucleic acid sequence-based amplification (NASBA), Helicase-dependent amplification and loop-mediated isothermal amplification. NAAT methods have largely displaced culture based detection for *C. trachomatis* methods not least because culture based methods involved the added complexity of requiring the use of mammalian cell or tissue culture. They involve detecting nucleic acids in a highly sensitive sequence-specific manner involving amplification of one or more target sequences using enzymes.

For further details of NAATs; the reader is referred to the following references which are incorporated by reference:

Nucleic Acid Sequence Based Amplification (NASBA)
  Compton J. Nucleic acid sequence-based amplification Nature 1991:350(6313):91-2
Transcription Mediated Amplification
  Wroblewski J. et al. Comparison of Transcription. Mediated Amplification and PCR Assay Results from Various Genital Specimen Types for Detection of *Mycoplasma genitalium*. J. Clin. Microbiol. 2006: 44(9):3306-3312
Ligase Chain Reaction
  Wiedmann M. et al. Ligase chain reaction (LCR) overview and Applications. PCR. Methods and Applications 1994 3(4)S51-64
Loop-Mediated Isothermal amplification of DNA
  Notomi et al. Loop-Mediated isothermal amplification of DNA. Nucleic Acids. Res. 2000 23 (12):E63.
Helicase-Dependent Amplification
  Vincent M. et al. Helicase-dependent isothermal DNA Amplification EMBO Rep. 2004 5(8) 795-800
Strand Displacement amplification
  Strand displacement amplification—an isothermal in vitro Amplification technique. Walker et al. Nucleic Acids Res. 1992. 20(7) 1691-1696
Recombinase-Polymerase Amplification (RPA)
  DNA Amplification and Detection Made Simple (Relatively). Hoff. M. Public Libr. Sic. 2006: 4(7): e222; and also U.S. Pat. No. 7,270,981.

Polymerase Chain Reaction (PCR)

PCR is a method of detecting nucleic acids in a highly sensitive sequence-specific manner involving amplification of one or more target sequences by using a thermostable polymerase enzyme and cycling the temperature conditions of the reaction.

In its simplest form a PCR reaction cycles through three stages: i) a denaturation stage occurring at a temperature of approximately 90-100° C. At this elevated temperature double-stranded DNA denatures or "melts" to form single-stranded DNA, ii) primer annealing at a typical temperature of 50-65° C. In this step the forward and reverse primers hybridize to the complimentary regions of any target present in the solution, and iii) extension typically occurring at 50-80° C. during which the polymerase chain reaction utilises deoxynucleotide triphosphates in the solution to extend the 3' end of the primers. Typically, the cycle is carried out 25-45 times. According to certain PCR protocols the annealing step and the extension step may be conflated so that the sample cycles through a two-step programme of 90° C. to 100° C. then 50° C. to 80° C. intervals. Theoretical calculations show that a 30 cycle PCR reaction can amplify a single target molecule 268,435,456 times. Because of inefficiencies in the amplification reaction, actual amplification may be less than this, but nevertheless the PCR reaction is typically able to amplify single or very low numbers of target molecules millions of times to a level at which they can be much more easily detected. PCR reactions rely on a thermostable DNA polymerase, for example, Taq polymerase isolated from the thermophilic bacterium *Thermus aquaticus*. Other thermostable DNA polymerases can be used in place of Taq, for example, Pfu polymerase isolated from *Pyrococcus furiosus* which has a proof-reading activity absent from Taq polymerase and is therefore a higher fidelity enzyme.

A review of the polymerase chain reaction is found in most molecular biology textbooks, see, for example, "Principles of Gene Manipulation—An Introduction to Genetic Engineering" by Old and Primrose, Blackwell Science Ltd which is incorporated herein by reference. There are a number of different "PCR formats". As a basic requirement, a PCR reaction requires a forward primer and a reverse primer designed to hybridize either side of the target sequence. The amplification reaction occurs in respect of the intervening sequence between the two primers. The detection of amplified PCR products may be carried out in a non-specific way which merely detects the presence of double-stranded nucleic acid (for example, by use of a double-stranded-DNA intercalating dye such as ethidium bromide or SYBR-green). Alternatively, a semi-specific detection of product may be carried out by resolving approximate molecular weight of the product, for example, by Carrying out an electrophoresis of the reaction products prior to detection. Alternatively, there are a number of sequence-specific detection methods which typically involve the hybridization of a sequence-specific nucleic acid probe to the amplified region or which measure the degradation of the probe concomitant with the amplification of the target sequence and make use of the nucleic acid exonuclease activity of the nucleic acid polymerase. PCR-based methods of detection for pathogenic agents typically offer the advantage of faster results than more traditional methods which usually involve culture and incubation over a number of days. A PCR result can be made available in a few hours or less.

SUMMARY OF INVENTION

According to a first aspect of the invention there is provided a method of detecting in a sample genetic material deriving from *Chlamydia trachomatis* comprising sequence-specific detection of a nucleic acid sequence, said nucleic acid sequence comprising at least 10 contiguous nucleotide residues contained in SEQ ID NO: 1

```
SEQ ID NO: 1:
atgaattcaa atatagaata taggcaatat cgtatagata tactgagctg ttttatctgc ttgctaatga tggtttggac
```

-continued
```
actagtcagc atcaagctag gagattctct aggaggcatc attcctggat gcttaggata cttactggct aaaaggaagc atcgccgtcc tgtccgctgg ttcttcctta cttttttctt tggcattgcc tctggaatct tccttgtcgt tcttcatcct aagcaaaagt aa
``` or its complement; wherein the sequence may be further mutated by up to 5 additions of residues, deletions of residues or substitutions of residues.

According to a second aspect of the invention there is provided a forward PCR primer comprising a nucleic acid sequence comprising between 17 and 34 contiguous nucleotide residues selected from SEQ ID NO: 15

```
SEQ ID NO: 15:
tgatg - g/c-t/a-t/a-t/a-g/c -g/c-a/t- cactagtc agcatcaagc taggagatt
``` wherein the sequence may be further mutated by up to 5 additions of residues, deletions of residues or substitutions of residues.

Alternatively, the sequence of the primer deriving from SEQ ID NO: 15 may be shorter (preferably between 12 and 22 or 19 and 29 residues in length) if steps are taken to increase the annealing temperature of the primer.

According to a third aspect of the invention there is provided a reverse PCR primer comprising a nucleic acid sequence comprising, between 15 and 31 contiguous nucleotide residues selected from SEQ ID NO: 16

```
SEQ ID NO: 16:
aaggaagatt ccagaggcaa tgccaaagaa aaaagt
``` wherein the sequence may be further mutated by up to 5 additions of residues, deletions of residues or substitutions of residues.

Alternatively, the sequence of the primer deriving from SEQ ID NO: 16 may be shorter (preferably between 10 and 20 or 16 and 26 residues in length) if steps are taken to increase the annealing temperature of the primer.

According to a fourth aspect of the invention there is provided a nucleic acid probe comprising a nucleic acid sequence, said nucleic acid sequence comprising between 18 and 28 nucleic acid residues given in SEQ ID NO: 4

```
                                           SEQ ID NO: 4
ccgtcctgtc cgctggttct tccttacttt ttt
``` or its complement; wherein the sequence may be further mutated by up to 0.5 additions of residues, deletions of residues or substitutions of residues.

Alternatively, the sequence of the probe deriving from SEQ ID NO: 4 may be shorter (preferably between 13 and 23 residues in length) if steps are taken to increase the annealing temperature of the probe.

According to a fifth aspect of the invention there is provided a PCR component comprising a forward PCR primer according to the invention and a reverse PCR primer according to the invention.

According to a sixth aspect of the invention there is provided a kit comprising a PCR component as according to the invention and instructions for carrying out a method according to the invention.

According to a seventh aspect of the invention there is provided a method of detecting in a sample genetic material deriving from *Pectobacterium atrosepticum* comprising sequence-specific detection of a nucleic acid sequence, contained in the chromosome of *Pectobacterium atrosepticum*.

According, respectively, to the eighth, ninth and tenth aspects of the invention there are separately provided forward PCR primers as defined as a "second forward PCR primer" in accordance with the fifth aspect of the invention; a reverse PCR primer as defined as a "second reverse PCR primer" in accordance with the fifth aspect of the invention; and a PCR probe as defined as a "second PCR probe" in accordance with the fifth aspect of the invention.

The invention also provides PCR components comprising any one or more forward PCR primer, reverse PCR primer or PCR probe in accordance with the eighth, ninth or tenth aspect of the invention in combination with one or more further components of a PCR reaction.

BRIEF DESCRIPTION OF THE DRAWINGS

FIGS. 1*a* to 1*c* show the results of Limit of Detection (LOD) determination experiments carried out for plasmid target amplicons 3, 5 and 7 as described in the examples.

FIGS. 2*a* to 2*c* show the results of Limit of Detection (LOD) determination experiments carried out for chromosomic target amplicons 9, 17 and 18 as described in the examples.

FIG. 2*d* shows the results of the chromosomal amplicon 17 [$Mg^{2+}$] optimisation experiment as described in the examples.

FIG. 3 shows the results of the chromosomal amplicon 17 experiments described in example 8.

FIG. 4 shows the effect of Internal Control primers and DNA on electrochemical detection of *Chlamydia trachomatis* amplicon generated using duplex PCR (Example 9). Error bars show the SD (n=3). The legend for each bar within each group of 4 is as in FIG. 5. The legend "ME17 primers+20 pg IC DNA" corresponds to the first bar in each group of 4. The legend "ME17 primers, no IC DNA" refers to the second bar in each group of four. The legend "ME17 and IC primers+200 μg IC DNA" refers to the third bar in each group of four. The legend "ME17 and IC primers; no IC DNA" refers to the fourth bar in each group of four.

FIG. 5 as FIG. 4, but for experiment carried out to detect internal control amplicons.

FIG. 6*a* shows an electrophoretic gel of amplification products of *Chlamydia trachomatis* without the Internal Control primer set. Lane 1=100 bp ladder; lanes 2 to 4=10,000 IFU reactions; lanes 5 to 7=1,000 IFU reactions; lanes 8 to 10=100 IFU reactions; lanes 11 to 13=10 IFU reactions; lanes 14 to 16=1 IFU reaction.

FIG. 6*b* as FIG. 6*a*, but lane 1=100 bp ladder and lanes 2 to 4=no IFU reactions.

FIG. 7*a* and FIG. 7*b* as FIGS. 6*a* and 6*b* but for reactions containing the Internal Control primer set.

FIG. 8 shows the results of electrochemical detection of samples amplified in duplex using *Chlamydia trachomatis* (CT, first bar of each pair) primers SEQ ID NOS: 17 and 19 and Internal Control (IC, second bar of each pair) primer set 200 pg of Internal Control DNA added in all cases. Error bars show the SD (n=3).

FIG. 9 shows the results of the comparative duplex experiments described in Example 10.

DEFINITIONS

Polymerase Chain Reaction (PCR)

As described in the background section, PCR is a technique widely used in molecular biology to amplify a segment of DNA by in vitro enzymatic replication. As the reaction progresses, the DNA generated by earlier replications are used as templates for later replications. This sets in motion a chain reaction in which DNA template is exponentially or approximately exponentially amplified. With PCR it is possible to amplify single or very few copies of nucleic acid across several orders of magnitude generating a Million or more copies which May be more easily detected. The basic PCR set-up requires the following components: i) a DNA template or target to be amplified; ii) a pair of primer's; the forward primer which is complementary to the DNA region at the 5' prime end of the target region and the reverse primer which is complementary to the DNA region at the 3' prime end of the target region; iii) a thermostable DNA polymerase, for example, Taq polymerase; iv) deoxynucleoside triphosphates (dNTPs). These are used as the building blocks from which the DNA polymerase synthesises the new DNA strand; v) a suitable buffer solution; vi) magnesium ions or other suitable cations; vii) monovalent potassium ions or other suitable cations.

A number of PCR variants exist, for example, multiplex PCR involves the simultaneous amplification of more than one target in a single sample container. Multiplex PCR includes duplex and triplex PCR reactions involving up to a dozen sets of primers acting independently.

Nested PCR is a technique which can be used to increase specificity of a PCR amplification reaction. Two sets of primers are used in two successive reactions. In the first one a pair of primers is used to generate DNA products in a less than completely specific fashion. Nevertheless, the first reaction increases the instance of the target sequence. The second reaction is more specific and amplifies a sequence nested within the first set of primers.

Quantitative PCR (QPCR) is used to measure or estimate the specific amount of target DNA in a sample. The normal PCR process may, under some circumstances, be approximately quantitative but the aim of true quantitative PCR is to run the amplification reaction or consider the results of the amplification reaction only within the phase of true exponential increase of product amount, thereby avoiding the later plateau phase of amplification. The amount of product in the exponential phase of amplification is much more proportional to the initial amount of target. Thermocyclers have been developed which can monitor the amount of product during amplification. One method currently used is quantitative real-time PCR which uses a fluorescent dye such as SYBR-green or fluorophore-containing DNA probes such as the proprietary TaqMan™ system to measure the amount of amplified product as the amplification progresses.

Hot-start PCR avoids a possible problem whereby the primers are able to bind at low temperatures to non-specific locations or even to each other. Hot-start PCR is based on the principle of releasing the primers for hybridization only when the reaction temperature is sufficiently high to prevent or reduce non-specific primer binding. The technique can be performed manually by heating the reaction components to the denaturation temperature, for example 94° C. before adding the polymerase or before adding the primers. Alternatively, specialised systems have been developed which inhibit the reaction until the temperature is raised by, for example, binding one or more of the components in an inactive form to be released on the raising of temperature.

Reverse transcriptase PCR (RT-PCR) is a method used to amplify RNA in which a PCR reaction is preceded by a reaction using reverse transcriptase to convert RNA to cDNA. The two reactions are sufficiently compatible that they can be run in the same tube and be carried out in the same thermal cycling instrument.

Methylation-specific PCR or (MSP) involves pre-treating the target DNA with sodium bisulphite which converts unmethylated cytosine units into uracil which is recognised by the DNA primers as thymine. Two amplifications are carried out on the modified DNA using primer sets which distinguish between the modified and unmodified templates. One primer set recognises DNA with cytosines and amplifies the previously unmethylated DNA and the other set recognises DNA with uracil or thymine to amplify methylated targets. The relative proportions of the two amplifications can be used to obtain information about the extent of methylation.

DETAILED DESCRIPTION OF THE INVENTION

Selection of *Chlamydia* Target Sequence

*Chlamydia trachomatis* contains genetic information on both a chromosome and a plasmid. The plasmid of *Chlamydia trachomatis* contains 8 open reading frames and because it is present in multiple copy number it is a favoured target for NAAT detection methods of the prior art. However, the inventors realised that many of those open reading frames contain a great deal of variability. At the very least single nucleotide polymorphisms (SNPs) were detected in open reading frames 2, 4, 7 and 8. Open reading frames 1 and 3 have been shown to contain both insertions and deletions. It was therefore decided that the target sequence for nucleic acid detection in accordance with the invention should come from the chromosomal sequence of *Chlamydia trachomatis*. The putative gene identified in SEQ ID NO:1, referred to herein as chromosomal sequence 17 and found on the chromosome of *Chlamydia* trachomatis was found to be most suitable for use in methods of the invention because it has low variability among *Chlamydia trachomatis* isolates, has low level of homology with non-*Chlamydia trachomatis* isolates and can surprisingly be detected by a PCR assay having an advantageous limit of detection (LOD) at least as good as plasmid targets despite its single copy number. Further details of selection of PCR primers for use in accordance with preferred aspects of the invention are given in the examples.

Chromosomal sequence 17 has been suggested to be a hypothetical membrane-associated protein but has yet to be given an official name. Its function in the organism is not important in so far as its proven suitability for use in accordance with the present invention is concerned.

According to a first aspect of the invention there is provided a method of detecting in a sample genetic material derived from *Chlamydia trachomatis* comprising sequence-specific detection of a nucleic acid sequence comprising at least 10 contiguous nucleic acid residues claimed in SEQ ID NO: 1

```
SEQ ID NO: 1:
atgaattcaa atatagaata taggcaatat cgtatagata tactgagctg ttttatctgc ttgctaatga tggtttggac actagtcagc atcaagctag gagattctct aggaggcatc
```

-continued

```
attcctggat gcttaggata cttactggct aaaaggaagc atcgccgtcc tgtccgctgg ttcttcctta ctttttttctt tggcattgcc tctggaatct tccttgtcgt tcttcatcct aagcaaaagt aa
``` or its complement; wherein the sequence may be further mutated by up to 5 additions of residues, deletions of residues or substitutions of residues.

According to certain embodiments it is preferred that the nucleic acid sequence comprises at least 15 contiguous nucleic acid residues from SEQ ID NO: 1.

According to certain preferred embodiments there may be 1, 2, 3 or 4 deletions of residues, substitutions of residues or additions of residues. According to certain preferred embodiments substitutions of residues are preferred over deletions of residues or additions of residues. According to certain preferred embodiments there are no substitutions, deletions or additions of residues. Similar preferred features in respect of further mutations apply to all other aspects of the invention.

Preferably said sequence-specific detection comprises carrying out a nucleic acid hybridisation step.

Preferably said sequence-specific detection comprises carrying out a nucleic acid hybridisation step followed by a step for detecting nucleic acid hybridisation.

Detection of Nucleic Acid Hybridization

Methods of detecting nucleic acid hybridization include methods of detecting nucleic acid hybridization in a non-sequence specific manner. These methods include the use of a nucleic acid intercalating dye, for example, ethidium bromide or SYBR-Green. These dyes increase their fluorescent signal when bound to double-stranded nucleic acid and may be detected by a standard fluorescence detection system. According to alternative embodiments the method of detecting nucleic acid hybridization may be a sequence-specific method, for example, labelled probes. One or more labelled probes may be hybridized to the target sequence in a sequence specific fashion or the target's sequence may be detected following hybridization to an immobilised complementary sequence (for example, on a DNA array or "chip"). Nucleic acid probes may be labelled fluorescently, radioactively, enzymatically or according to certain preferred embodiments of the invention, electrochemically. Electrochemical labelling using the electrochemical labels disclosed in this document is particularly preferred.

According to certain preferred embodiments the method of detecting in a sample genetic material deriving from *Chlamydia trachomatis* comprises hybridization of genetic material deriving from *Chlamydia trachomatis* to a nucleic acid sequence comprising at least 15 contiguous nucleic acid residues containing SEQ ID NO: 4

```
SEQ ID NO: 4:
ccgtcctgtc cgctggttct tccttacttt ttt
``` or its complement; wherein the sequence may be mutated by up to 5 additions of residues, deletions of residues or substitutions of residues. According to certain embodiments there are 1, 2, 3 or 4 additions of residues, deletions of residues or substitutions of residues.

According to certain preferred embodiments the method comprises hybridization of genetic material deriving from

*Chlamydia trachomatis* to a nucleic acid sequence comprising the sequence in SEQ ID NO: 5

```
SEQ ID NO: 5:
ctgtccgctg gttcttcctt act
``` or its complement; wherein the sequence may be further mutated by up to 5 additions of residues, deletions of residues or substitutions of residues.

According to certain preferred embodiments, further mutations are as defined above.

According to certain preferred embodiments the sequence-specific detection follows amplification of the nucleic acid to be detected using PCR, transcription-mediated amplification, nucleic acid sequence-based amplification (NASBA), helicase-dependent amplification, recombinase polymerase amplification, strand displacement amplification or loop-mediated isothermal amplification. By using a detection method wherein sequence specific detection follows amplification of the nucleic acid to be detected, greater sensitivities and specificities in the detection method may be obtained.

preferably the sequence specific detection method follows amplification of the nucleic acid to be detected—that amplification being by use of a PCR.

Polymerase Chain Reaction

Polymerase chain reaction involves the use of a forward PCR primer and a reverse PCR primer. According to certain preferred embodiments of the first aspect of the invention said polymerase chain reaction involves use of a forward PCR primer and a reverse PCR primer wherein:

a) said forward PCR primer comprises a nucleotide sequence comprising between 17 and 34 (for example between 24 and 34) contiguous nucleotide residues selected from SEQ ID NO: 15;

```
tgatg - g/c-t/a-t/a-t/a-g/c -g/c-a/t-cactagtc agcatcaagc taggagatt
``` and b) said reverse PCR primer comprises a nucleic acid sequence comprising between 15 and 31 (for example between 21 and 31) contiguous nucleotide residues selected from SEQ ID NO: 16;

```
SEQ ID NO: 16:
aaggaagatt ccagaggcaa tgccaaagaa aaaagt
``` or wherein said forward PCR primer comprises a nucleic acid sequence that is the complement of the reverse primer as defined in part b) above and said reverse PCR primer comprises a nucleic acid sequence that is the complement of the forward primer as defined in part a) above; wherein the sequences may be further mutated by up to 5 additions of residues, deletions of residues or substitutions of residues.

For example, said polymerase chain reaction may involve use of a forward PCR primer and a reverse PCR primer wherein:

a) said forward PCR primer comprises a nucleic acid sequence comprising between 17 and 27 contiguous nucleotide residues selected from SEQ ID NO: 2;

```
SEQ ID NO: 2:
ttggacacta gtcagcatca agctaggaga tt;
``` and b) said reverse PCR primer comprises a nucleic acid sequence comprising between 15 and 25 contiguous nucleotide residues selected from SEQ ID NO: 3

```
SEQ ID NO: 3:
gaagattcca gaggcaatgc caaagaaaaa;
``` or wherein said forward PCR primer comprises a nucleic acid sequence that is the complement of the reverse primer as defined in part b) above and said reverse PCR primer comprises a nucleic acid sequence that is the complement of the forward primer as defined in part a) above; wherein the sequences may be further mutated by up to 5 additions of residues, deletions of residues or substitutions of residues.

Further mutations may be as defined above. In certain embodiments the forward PCR primer may be as defined with respect to the second aspect of the invention and the reverse PCR primer may be as defined with respect to the third aspect of the invention.

According to certain preferred embodiments the forward PCR primer comprises a nucleic acid having the sequence given in SEQ ID NO: 17, SEQ ID NO: 18 or SEQ ID NO: 6

```
SEQ ID NO: 6:
cactagtcag catcaagcta gg;

SEQ ID NO: 17:
caaacctcac tagtcagcat caagctagg;

SEQ ID NO: 18:
gtttggacac tagtcagcat caagctagg;
``` and the reverse PCR primer comprises a nucleic acid having the sequence given in SEQ ID NO: 19 or SEQ ID NO: 7

```
SEQ ID NO: 7:
ttccagaggc aatgccaaag;

SEQ ID NO: 19
agattccaga ggcaatgcca aagaaa
```

According to certain embodiments one or both of the PCR primers may be labelled to assist detection of hybridization. The label may be a fluorescence label, a radioactive label, an enzymatically active label or an electrochemically active label. The primer and label may be arranged such that their detectable signal increases following hybridization or following degradation by the exonuclease activity of the DNA polymerase used in the PCR reaction. For example, the label may be applied to a PCR primer to which a quencher moiety has also been added. Degradation of the PCR primer will result in the quencher moiety and the label becoming separated from each other and the quenching activity of the quencher on the label becoming diminished.

Nucleic Acid Probes

Probes

A nucleic acid probe may be used to detect in a sequence-specific fashion the products of a PCR reaction. Typically, such a probe is designed to anneal to the target sequence at a position intermediate between the positions at which the primers anneal. The probe may be labelled to assist in its detection, for example, a fluorophore, a radioactive label, an electrochemically active label or an enzymatic label. The label may be linked directly to the nucleic acid or by means of a linker moiety. The probes of the present invention are particularly suitable for the TaqMan PCR format. TaqMan is a method of real time quantitative PCR available from Life Technologies Inc. In the TaqMan format real time measurements of accumulation of the PCR product during the experimental phase of the amplification is taken. This is carried out in order to determine a threshold cycle, i.e., the number of PCR cycles at which a threshold level of signal is detected. The PCR probes in a TaqMan format are fluorescently labelled and complimentary to a segment of approximately 20 to 60 nucleotides within the DNA template located between the two primers. Suitable fluorescent labels for use in a TaqMan system include 6 carboxyfluorescein (FAM) or tetrachlorofluorescein (TET). The TaqMan probe is typically labelled with such a fluorophore and also labelled with a quencher molecule, for example, tetramethylrhodamine (TAMRA). The close proximity between the fluorophore and the quencher inhibits the fluorescence of the fluorochrome. However during the primer extension phase of the PCR reaction the Taq polymerase also exhibits 5' to 3' exonuclease activity which degrades the portion of the probe that is already annealed to the template. Degradation of the probe releases fluorochrome from it. The fluorochrome is no longer in close proximity to the quencher, thus the quenching effect is diminished and the fluorescent signal given off by the fluorochrome increases and may be detected.

According to certain embodiments of the invention the polymerase chain reaction involves the use of a nucleic acid probe comprising a nucleic acid sequence. Said nucleic acid sequence comprising between 18 and 28 nucleic acid residues given in SEQ ID NO: 4

SEQ ID NO: 4:
ccgtcctgtc cgctggttct tccttactt ttt or its complement; wherein the sequence may be further mutated by up to 5 additions of residues, deletions of residues or substitutions of residues defined above.

According to certain embodiments the nucleic acid sequence, comprises between 19 and 27 nucleic acid residues given in SEQ ID NO: 4, more preferably between 20 and 26 nucleic acid residues, more preferably between 21 and 25 nucleic acid residues, more preferably, between 22 and 24 nucleic acid residues, most preferably 23 nucleic acid residues.

Preferably, the nucleic acid probe comprises a nucleic acid sequence given in SEQ ID NO: 5

SEQ ID NO: 5:
ctgtccgctg gttcttcctt act

According to certain embodiments the nucleic acid probe may be labelled, for example, fluorescently, radioactively, enzymatically or most preferably with an electrochemically active label. The electrochemically active labels disclosed therein are especially preferred.

According to a second aspect of the invention there is provided a forward PCR primer comprising a nucleic acid sequence comprising between 17 and 34 (for example, 24 and 34) contiguous nucleotide resides selected from SEQ ID NO: 15;

SEQ ID NO: 15:
tgatg - g/c-t/a-t/a-t/a-g/c -g/c-a/t- cactagtc agcatcaagc taggagatt wherein the sequence may be further mutated by up to 5 additions of residues, deletions of residues or substitutions of residues said further mutations being optionally as defined above.

According to certain embodiments, there is provided a forward PCR primer comprising a nucleic acid sequence comprising between 17 and 27 contiguous nucleotide residues selected from SEQ ID NO: 2;

SEQ ID NO: 2:
ttggacacta gtcagcatca agctaggaga tt;

wherein the sequence may be further mutated by up to 5 additions of residues, deletions of residues or substitutions of residues said further mutations being optionally as defined above.

According to certain embodiments, there is provided a forward PCR primer comprising a nucleic acid sequence comprising between 24 and 34 contiguous nucleotide residues selected from SEQ ID NO: 20;

SEQ ID NO: 20:
tgatgcaaac ctcactagtc agcatcaagc taggagatt;

wherein the sequence may be further mutated by up to 5 additions of residues, deletions of residues or substitutions of residues said further mutations being optionally as defined above.

According to certain embodiments, there is provided a forward PCR primer comprising a nucleic acid sequence comprising between 24 and 24 contiguous nucleotide residues selected from SEQ ID NO: 21;

SEQ ID NO: 21:
tgatggtttg gacactagtc agcatcaagc tagg agatt;

wherein the sequence may be further mutated by up to 5 additions of residues, deletions of residues or substitutions of residues said further mutations being optionally as defined above.

According to certain embodiments the nucleic acid sequence comprises between 18 and 26, between 19 and 25, between 20 and 24, between 21 and 23, most preferably 22 residues or between 25 and 33, between 26 and 32, between 27 and 31, between 28 and 30 most preferably 29 residues. According to certain preferred embodiments the forward PCR primer comprises a nucleic acid having sequence given in SEQ ID NO: 17, SEQ ID NO: 18 or SEQ ID NO: 6.

SEQ ID NO: 6:
cactagtcag catcaagcta gg;

SEQ ID NO: 17:
caaacctcac tagtcagcat caagctagg

SEQ ID NO: 18:
gtttggacac tagtcagcat caagctagg.

According to a third aspect of the invention there is provided a reverse PCR primer comprising a nucleic acid sequence comprising a nucleic acid sequence comprising between 15 and 31 (for example between 21 and 31) contiguous nucleotide residues selected from SEQ ID NO: 16;

```
SEQ ID NO: 16:
aaggaagatt ccagaggcaa tgccaaagaa aaaagt;
```

Wherein the sequence may be further mutated by up to 5 additions of residues, deletions of residues. Or substitutions of residues, said further mutations being optionally as defined above.

According to certain embodiments there is provided a reverse PCR primer comprising a nucleic acid sequence comprising between 15 and 25 contiguous nucleotide residues selected from SEQ NO: 3

```
SEQ ID NO: 3:
gaagattcca gaggcaatgc caaagaaaaa;
``` wherein the sequence may be further mutated by up to 5 additions of residues, deletions of residues or substitutions of residues said further mutations being optionally as defined above.

According to certain embodiments the nucleic acid sequence comprises between 22 and 30 contiguous nucleotide residues selected from SEQ ID NO: 16. More preferably between 23 and 29, more preferably between 24 and 28, more preferably between 25 and 27, most preferable 26 residues.

According to certain embodiments the nucleic acid sequence comprises between 16 and 24 contiguous nucleotide residues selected from SEQ ID NO: 3. More preferably between 17 and 23 more preferably between 18 and 22, more preferably between 19 and 21, most preferably 20 residues.

According to certain embodiments the numbers and types of additions, deletions and substitutions of residues may be as defined above in reference to the forward PCR primer.

According to certain preferred embodiments the reverse PCR primer comprises a nucleic acid sequence given in SEQ ID NO: 19 or SEQ ID NO: 7

```
SEQ ID NO: 7:
ttccagaggc aatgcdaaag;

SEQ ID NO: 19:
agattccaga ggcaatgcca aagaaa
```

According to a fourth aspect of the invention there is provided a nucleic acid probe comprising a nucleic acid sequence, said nucleic acid sequence comprising between 18 and 28 nucleic acid residues given in SEQ ID NO: 4

```
SEQ ID NO: 4:
ccgtcctgtc cgctggttct tccttacttt ttt
``` or its complement; wherein the sequence may be further mutated by up to 5 additions of residues, deletions of residues or substitutions of residues.

The number and type of additions, deletions, substitutions of residues may be as defined above in reference to the primers of the invention. The nucleic acid probe according to certain preferred embodiments comprises between 18 and 27, between 19 and 26, between 20 and 25, between 21 and 24, between 22 and 23, most preferably 23 residues from SEQ ID NO: 4.

According to certain preferred embodiments a nucleic acid probe of the invention comprises a nucleic acid sequence given in SEQ ID NO: 5

```
SEQ ID NO: 5:
ctgtccgctg gttcttcctt act.
```

According to a fifth aspect of the invention there is provided a PCR component comprising a forward PCR primer of the invention and a reverse PCR primer according to the invention. According, to certain preferred embodiments the PCR component further comprises a nucleic acid probe according to the invention.

Internal Controls

Typically assay internal controls for a PCR or similar assay consist of single-stranded DNA oligonucleotides. These can be simply manufactured and immobilised onto a sample carrier or added to a component of the PCR reaction. However, the methods of the present invention may be preceded by sample preparation steps which may involved purifying elementary bodies or clinically derived *Chlamydia*-containing material and purifying genomic DNA from them. A number of commercially available DNA purification methods and kits are available, for example, the Promega Wizard System. These bacterial lysis and DNA Purification systems involve the use of a chaotropic salt containing solution with DNA binding to a membrane, for example, a silica-based membrane followed by the removal of the remaining lysate and washing to remove contaminants. The purified bacterial genomic DNA is then recovered from the membrane for use in the downstream detection assay, for example, an assay in accordance with the first aspect of the present invention. Such purification methods are unlikely to co-purify short single-stranded DNA, oligonucleotide based internal control sequences. For example, the Promega Wizard kit states that their purification protocol has a 50 kb size cut off. The inventor therefore realises that it would be advantageous to provide an internal control which would co-purify with the *Chlamydia* genomic DNA contained in the sample. A possible solution is to use as an internal control a genomic DNA from another bacterial species using the same lysis in isolation conditions required to isolate genomic DNA from *Chlamydia*. Because of safety considerations the source of the internal control should ideally be derived from a non-pathogenic bacterium. Also it should be not normally be readily found in humans and should be easily culturable in a laboratory. The present invention involves the use of genomic DNA as in internal control which has been derived from Pectobacterium atrosepticum. This is because *P. atrosepticum* is culturable, widely-available and DNA isolated from it is easily co-purified with that derived from *Chlamydia*. It has only one chromosome and possesses many genes which appear unique to the species. Moreover, there are no reported cases of human infection with this species (it is a plant pathogen which causes soft rot and black leg of potatoes in temperate regions) which means it is unlikely to be found at anatomical sites or in clinical samples. For the avoidance of doubt it should be noted that Pectobacterium atrosepticum was previously known as *Erwinia carotovora* subsp. *atroseptica*. According to certain preferred embodiments, according to the fifth aspect of the invention the PCR component further comprises genomic DNA derived from *Pectobacterium atrosepticium* for use as an internal positive control. Preferably, it is of the strain ATCC BAA-672.

A PCR component according to the invention preferably comprise a second forward PCR primer and a second reverse PCR primer wherein said primers are designed to hybridize to nucleic acid sequences found within a nucleic acid sequence of SEQ ID NO: 8

```
SEQ ID NO: 8:
ctaccgtgta gggtcatagg cattgacctc atggctccac ggaatcgtgc gatcgtcaac tgcgacgtgc cattcacagt gcgtaagagc accgcgaatc tcggataaac actggcacca gtgctgtacg ccaatccaga ttgcttcttc ctcgctgtcg ggaagtttgg ttgaaccgga gagcacgatc cctttcctaa agacgttacc gattttcaca ttgagggcga aatcaaagga ttcccagttc aggcctgtac ccgtcgtcag atatttctca atttggtcat taacagaatg gcgttggacg atctccttca cggcagatat ttctttctgg ctcagggatt ttttacgtcg agcggtgtaa tagagcgaaa ttgccac;
``` or its complement wherein the sequence may be further mutated by up to 5 additions of residues; deletions of residues or substitutions of residues as defined, in number and type above in reference to PCR primers according to a first or second aspect of the invention.

The second forward PCR primer preferably comprises a nucleic acid sequence, comprising between 13 and 23 contiguous nucleic acid residues selected from SEQ ID NO: 9

```
SEQ ID NO: 9:
ctcgctgtcg ggaagtttgg ttgaaccg;
```

The second reverse PCR primer preferably comprises a nucleic acid sequence comprising between 15 and 25 contiguous nucleic acid residues selected from SEQ ID NO: 10

```
SEQ ID NO: 10:
acaggcctga actgggaatc ctttgatttc;
```

Alternatively said second forward PCR primer comprises a nucleic acid sequence that is a complement of the reverse primer as defined above and said second reverse PCR primer comprises a nucleic acid sequence that is the complement of the forward primer as defined above; wherein the sequences may be further mutated by up to 5 additions of residues, deletions of residues or substitutions of residues as defined in number and type above in reference to primers in accordance with the first or second aspect of the invention. The second forward PCR primer preferably comprises between 14 and 22 contiguous nucleic acid residues selected from SEQ ID NO: 9, more preferably between 15 and 21, more preferably between 16 and 20, more preferably between 17 and 19; most preferably 18 contiguous nucleic acid residues selected from SEQ ID NO: 9.

The second reverse PCR primer preferably comprises between 16 and 24 contiguous nucleic acid residues selected from SEQ ID NO: 10, most preferably between 17 and 23, more preferably between 18 and 22, more preferably between 19 and 21, most preferably 20 contiguous nucleic acid sequences selected from SEQ ID NO: 10.

According to certain preferred embodiments the second forward PCR primer comprises a nucleic acid sequence as given in SEQ ID NO: 11

```
SEQ ID NO: 11:
tgtcgggaag tttggttg
``` and the second reverse PCR primer comprises a nucleic acid having the sequence given in SEQ ID NO: 12

```
SEQ ID NO: 12:
cctgaactgg gaatcctttg
```

The PCR component according to certain, embodiments contains a second nucleic acid probe comprising a nucleic acid sequence, said nucleic acid sequence comprising between 18 and 28, more preferably between 19 and 27, more preferably between 20 and 26, more preferably between 21 and 25, more preferably between 22 and 24, most preferably 23 nucleic acid residues given in SEQ ID NO: 13

```
SEQ ID NO: 13:
ggagagcacg atccctttcc taaagacgtt acc
``` or its complement wherein sequence may be further mutated by up to 5 additions of residues, deletions of residues or substitutions of residues as defined in type and number above in reference to the first nucleic acid probe according to the third aspect of the invention.

According to certain preferred embodiments the nucleic acid probe comprises a nucleic acid sequence given in SEQ ID NO: 14

```
SEQ ID NO: 14:
gcacgatccc tttcctaaag acg
```

The present invention also contemplates products and methods relating to an internal control comprising *Pectobacterium atrosepticum* in the absence of products and methods for detection of *Chlamydia trachomatis* (ie for use as an internal control for the detection of nucleic acids other than those from *Chlamydia trachomatis*). Specifically, the invention contemplates a forward PCR primer and further contemplates a second PCR primer wherein said primers are designed to hybridise to a target nucleic acid sequence found within the genomic DNA of *Pectobacterium atrosepticum*. Preferably the primers are designed to hybridise the target nucleic acid sequence found within the nucleic acid sequence SEQ ID NO: 8

```
SEQ ID NO: 8:
ctaccgtgta gggtcatagg cattgacctc atggctccac ggaatcgtgc gatcgtcaac tgcgacgtgc cattcacagt gcgtaagagc accgcgaatc tcggataaac actggcacca gtgctgtacg ccaatccaga ttgcttcttc ctcgctgtcg ggaagtttgg ttgaaccgga gagcacgatc cctttcctaa agacgttacc gattttcaca ttgagggcga aatcaaagga ttcccagttc aggcctgtac ccgtcgtcag atatttctca atttggtcat taacagaatg gcgttggacg atctccttca cggcagatat ctctttctgg ctcagggatt ttttacgtcg agcggtgtaa tagagcgaaa ttgccac;
``` or its complement; wherein the sequence may be further mutated by up to 5 additions of residues, deletions of residues or substitutions of residues the type and number of additions, deletions or substitutions being as defined elsewhere in this specification.

Further features of the second forward PCR primer and the second reverse PCR primer may preferably be as defined herein in relation to other aspects of the invention. The invention also contemplates a nucleic acid probe for detection of the *Pectobacterium atrosepticum* internal positive control having features as defined in reference to other aspects of the invention. The invention also contemplates a method of detecting a signal from an internal positive control comprising *Pectobacterium atrosepticum* comprising use of *Pectobacterium atrosepticum* primers, an optional probe and incorporating any of the features disclosed herein in reference to other methods of the invention. A method of detecting the signal from an internal positive control comprising *Pectobacterium atrosepticum* preferably is preceded by a method of obtaining genomic DNA from *Pectobacterium atrosepticum* comprising lysis of whole *Pectobacterium atrosepticum* bacterial cells using chaotropic salts and optionally a silica-based membrane as described herein.

Kit

According to a sixth aspect of the invention there is provided a kit comprising a PCR component according to the fifth aspect of the invention or a PCR primer or probe according to eighth, ninth or tenth and instructions for carrying out a method according to the first aspect of the invention. A kit may contain further components for example sample vessels, packaging, PCR enzymes, amplification pre-cursors, sample tubes or detection instruments;

Internal Positive Controls

According to certain preferred embodiments a PCR component of the fifth aspect of the invention further comprises genomic DNA derived from *Pectobacterium atrosepticium* for use as an internal positive control. The method of detection may be as described herein in reference to other aspects of the invention or may involve using compounds or products described herein in reference to other aspects of the invention.

According to a seventh aspect of the invention there is provided a method of detecting in a sample genetic material deriving from *Pectobacterium atrosepticium* comprising sequence-specific detection of a nucleic acid sequence, contained in the chromosome of *Pectobacterium atrosepticium*. Said method may incorporate any feature disclosed in relation to other aspects of the invention and may optionally further comprise the extraction of genomic DNA from a sample said genomic DNA being that of *Pectobacterium atrosepticium* (optionally introduced to the sample as an internal control). Said extraction may be concomitant with the extraction of genomic DNA from a second organism (for example a bacterial pathogen) of interest.

According, respectively, to the eighth, ninth and tenth aspects of the invention there are separately provided forward PCR primers as defined as a "second forward PCR primer" in accordance with the fifth aspect of the invention; a reverse PCR primer as defined as a "second reverse PCR primer" in accordance with the fifth aspect of the invention; and a PCR probe as defined as a "second PCR probe" in accordance with the fifth aspect of the invention.

The invention also provides PCR components comprising any one or more forward PCR primer, reverse PCR primer or PCR probe in accordance with the eighth, ninth or tenth aspect of the invention in combination with one or more further components of a PCR reaction.

Preferred or optional features described in relation to the first to sixth aspect of the invention may optionally be incorporated into the seventh to tenth and into other aspects of the invention also.

Labels

The probes and/or primers may be linked to a label to assist their detection. That label may be radioactive, enzymatically active, fluorescently active or electrochemically active. According to embodiments Wherein there are components for the detection of nucleic acid deriving from *Chlamydia trachomatis* and also components for the detection of nucleic acids deriving from the internal positive control or wherein there is a method of simultaneous detection of the two nucleic acids, the labels used to assist in the detection of the internal positive control and in the detection of nucleic acid deriving from *Chlamydia trachomatis* are preferably distinguishable from each other, for example, they may be different fluorochromes or they may be different electrochemically active agents or electrochemically active labels providing electrochemically distinguishable activity.

The present invention is especially suitable for use with electrochemically labelled probes and/or primers. In particular, the electrochemical label may include those comprising metallo-carbocyclic pi complexes, that is organic complexes with partially or fully delocalized pi electrons. Suitable markers include those comprising sandwich compounds in which two carbocyclic rings are parallel, and also bent sandwiches (angular compounds) and monocyclopentadienyls. Preferably, the electrochemically active markers are metallocenyl labels. More preferably they are ferrocenyl labels.

Ferrocenyl and metallocenyl labels used in the probes according to the invention may advantageously be N-substituted ferrocene or metallocene carboxamides. The ferrocene or metallocene ring, which constitutes the labelling moiety, may be unsubstituted. If desired, the ferrocene or metallocene ring may be substituted by one or more substituents, the nature and location of which are selected so as to influence in a desired manner the redox characteristics of the ferrocene or metallocene moiety. The ferrocene or metallocene ring may additionally or instead be substituted by any ring substituents that do not materially reduce the electrochemical sensitivity of the label. The ferrocene or metallocene carboxamide moiety may be linked via the carboxamide nitrogen to the nucleotide or oligonucleotide. Linkage to the nucleotide or oligonucleotide is preferably via a phosphate group or via the base of the nucleotide. Both methods of linkage permit the label to be attached via any nucleotide along the length of the oligonucleotide. However if linkage is via a phosphate group it is advantageously via a 3' or 5' terminal phosphate group so as to minimise the likelihood that such linkage will sterically hinder Watson-Crick hybridization of the oligonucleotide or affect nuclease activity. Linkage via a region of the base not involved in Watson-Crick base pairing is predicted to be less disruptive of such base pairing. Therefore linkage via the base may be more suitable for labelling at non-terminal oligonucleotide sites. The label oligonucleotide may have a linker moiety between the oligonucleotide and the labelling moiety. Preferably, the labelled oligonucleotides have a ferrocenyl labelling moiety which is linked to the oligonucleotide by a linker moiety.

There may be used any suitable linker moiety. Suitable linker moieties may comprise an aliphatic chain which may be linear or branched, and saturated or unsaturated. Advantageously, the linker moiety is a linear or branched aliphatic chain having from 4 to 20 carbon atoms, and preferably from 6 to 16, especially from 8 to 14 atoms, especially 12 carbon atoms. The alkylene chains may be substituted by any substituent or may be interrupted by any atom or moiety provided that any such substituent, atom or moiety does not materially reduce the electrochemical sensitivity of the label. Illustrative, of the ferrocenyl labels which may be used in accordance with the invention are those in Formulae I to III. Molecules of formula Ia to IIIa are oligonucleotides labelled with the corresponding ferrocenyl labels. Formula IV is illustrative of a ferrocenyl label which may be attached via a nucleotide base, the amino-modified thymine base being included in Formula IV for the purposes of illustration.

I

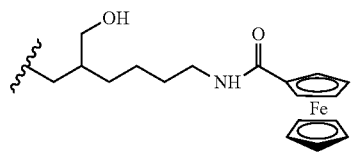

Ia

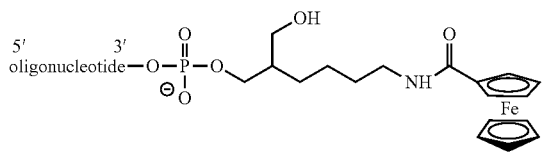

II

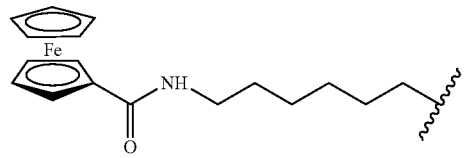

IIa

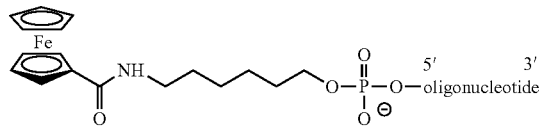

III

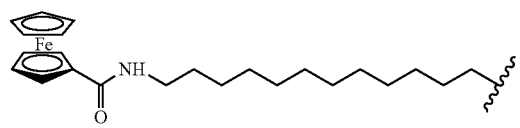

IIIa

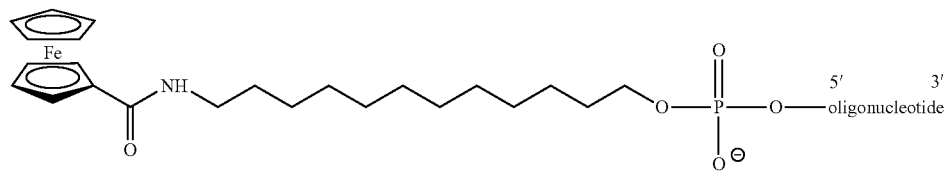

IV

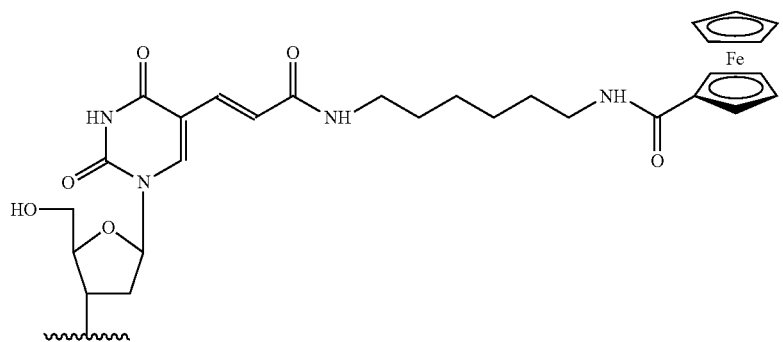

-continued

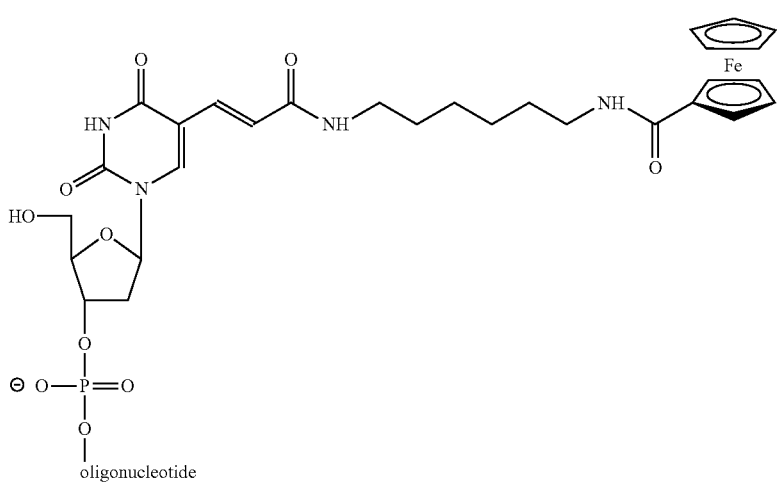

IVa

The ferrocene labelled probes may be made by any suitable method. By way of example, the oligonucleotide may be an oligonucleotide modified by introduction of a radical having a terminal amino group. Illustrative of such amino-modified nucleotides is the modified nucleotide of Formula V. The ferrocene may then be incorporated by reaction of the amino-modified nucleotide with the N-hydroxy-succinimide ester of ferrocene carboxylic acid (Formula VI) to obtain ferrocene labelled oligonucleotide.

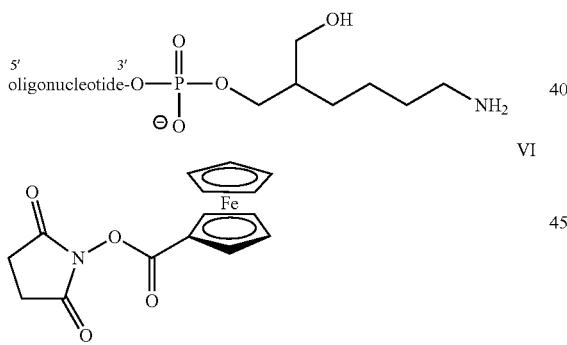

V

VI

In an alternative method, ferrocene labelled oligonucleotides may be prepared by addition of the ferrocene moiety during solid phase oligonucleotide synthesis. Ferrocene labels can be introduced into an oligonucleotide during solid phase synthesis by two general methods: Firstly, addition of the olignucleotide at the 3' end of the oligonucleotide requires the use of a suitable resin. Such a resin is labelled with a ferrocene derivative. Addition of ferrocene at an internal site, or at the 5' end of an oligonucleotide requires the use of a coupling reagent suitable for coupling with a solid support bound oligonucleotide, for example a ferrocenyl derivative phosphoramidite, for example as shown as formula IX or X.

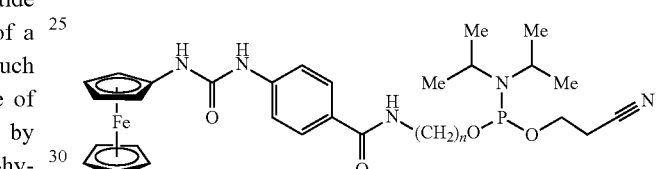

IX

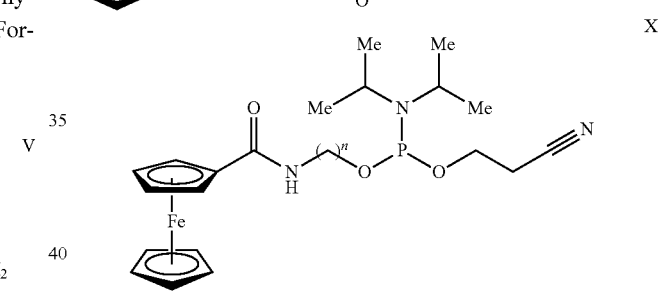

X

According to certain specific embodiments the electrochemically active label may be a compound of:

$$\text{Mc-NR'} - \text{C}(=\text{O}) - \text{X} - (\text{Ar})_n - (\text{L})_m - \text{R}$$ XI Wherein
Mc is a metallocenyl group in which each ring may independently be substituted or unsubstituted,
the metallocenyl group comprises a metal ion M selected from the group consisting of iron, chromium, cobalt, osmium, ruthenium, nickel or titanium,
R' is H or lower alkyl,
X is either NR' or O,
Ar is a substituted or unsubstituted aryl group,
n is 0 or 1,
L is a linker group,
m is 0 or 1, and
R represents a moiety to be labelled.

The Mc group may be substituted by one or more groups selected lower alkyl (for example C1 to C4 alkyl), lower alkyl substituted with a hydroxy, halo, cyano, oxo, amino, ester amido or a further metallocene group, lower alkenyl, lower alkenyl substituted with a hydroxy, halo; cyano, oxo, amino, ester, amido or a further metallocene group, aryl, aryl substituted with a hydroxy, halo; cyano, oxo; amino, ester, amido or a further metallocene group. The further metallocene group may be substituted in the same way as the Mc group with the exception that the total number Mc groups in the molecule of the invention preferably does not exceed four. Preferably, the Mc group is unsubstituted.

Preferably, M is an ion selected from iron, osmium or ruthenium. Most preferably, M is an iron ion. When M is an iron ion, Mc is a ferrocene.

Lower alkyl is preferably C1 to C4 alkyl. Preferably, R' is H. Each R' has an identity separate from the other R'.

Preferably X is NH.

The Ar group may be substituted by one or more groups selected lower alkyl (for example $C_1$ to $C_4$ alkyl), lower alkyl substituted with a hydroxy, halo, cyano, oxo, amino, ester or amido group, lower alkenyl, lower alkenyl substituted with a hydroxy, halo, cyano, oxo, amino, ester or amido group, aryl or aryl substituted with a hydroxy, halo, cyano, oxo, amino, ester or amido group. Preferably, the Ar group is unsubstituted.

Preferably, n=1. Preferably, m=1.

Suitable linker groups L may comprise an aliphatic chain which may be linear or branched, and saturated or unsaturated. Advantageously, the linker moiety is a linear or branched aliphatic chain having from 4 to 20 carbon atoms, and preferably from 6 to 16, especially from 8 to 14 atoms, more especially 12 carbon atoms. The alkylene chains may be substituted by any substituent or may be interrupted by any atom or moiety provided that any such substituent, atom or moiety does not materially reduce the electrochemical sensitivity of the label.

The compound of the invention may comprise more than one metallocene groups. In the compound of, the invention, the metallocene group may be substituted by any other electrochemically active marker group. The compound may be one which is electrochemically active or becomes electrochemically active following partial cleavage.

Preferably, the moiety to be labelled is an amino acid, a nucleotide, an oligonucleotide, a polynucleotide, a nucleoside, a sugar, a carbohydrate, a peptide, a protein or a derivative of any of those molecules. In a preferred embodiment, R is a nucleotide or an oligonucleotide. The nucleotide may be selected from adenosine, thymidine, guanosine, cytidine, or uridine. Preferably the nucleotide is attached through a group attached to the ribose or deoxyribose group of the nucleotide, for example in the 2', 3' or 5' position. Most preferably, the nucleotide is attached at the 3' or 5' position, for example at the 5' position. Preferably, the attachment at the 2', 3" or 5' position is through an oxygen or a nitrogen atom.

The labeling reagent may be attached directly or via a linker. The linker may be attached first to the labeling reagent or to the molecule to be labelled. If the linker is first attached to the Molecule to be labelled it may comprise a group, for example, an amino or a thiol group, that will assist in the labeling reaction. An amino group is preferred.

The nucleotide or an oligonucleotide is preferably labelled, to the 3' or 5' end. The oligonucleotide may be amino-modified to assist with the labeling reaction. Amino-modified oligonucleotides may be synthesized by standard techniques and are available from a wide range of commercial sources for example from Oswel Scientific (Southampton, UK). The amino-modified oligonucleotide may also incorporate a linker motif, for example, the modification may be the addition of 5' aminohexyl or 3' aminohexyl or a 5'-C12 amino-group. A labelled molecule of interest preferably comprises a linker.

In the case of an oligonucleotide, the sequence of the oligonucleotide portion of the molecule is preferably such that the molecule is able to hybridize with a complementary target sequence and thus be used as a probe in a molecular biological technique, for example, one of the nucleic acid detection or qualification techniques disclosed in this specification.

Labelled biological molecules in accordance with the invention may be electrochemically active in either digested or non-digested states. Ideally the extent of electrochemical activity will vary in dependence on the extent of digestion.

Formula VIII illustrates a possible mode of attachment of the novel electrochemically active marker to an oligonucleotide. The molecule of formula VIII may be obtained by reacting a 5'-aminohexyl modified oligonucleotide with the molecule shown in formula VII.

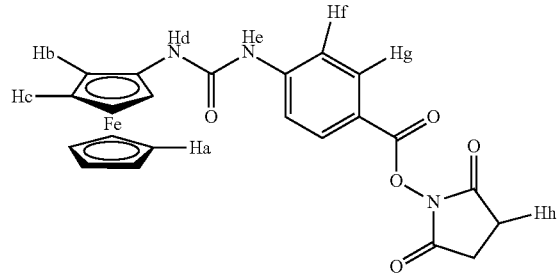

VII

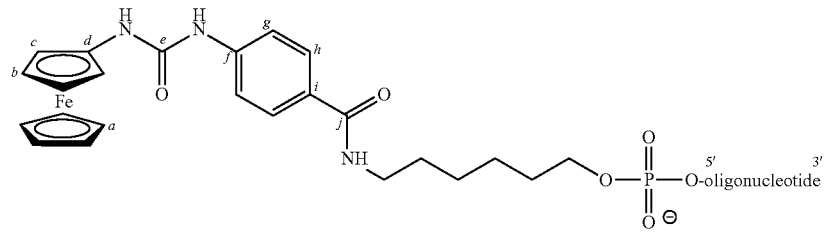

VIII

Details of N-hydroxysuccinimide ester of 4-(3'-ferrocenylureido)-1-benzoic acid and details of the use of said compound to label oligonucleotides are provided in Examples 7 and 8. It will however be apparent to the skilled person that such a label may be attached to an oligonucleotide at any suitable position and that attachment is not limited to the 5' end of said oligonucleotide. For details of synthesis and attachment of the above electrochemical labels, readers are referred to EP1481 083 which is hereby incorporated by reference.

Use of Shorter Primers and Probes

According to certain embodiments of all of the aspects of the invention relating to hybridization, primers and probes may be shorter than those specified above particularly if steps are taken to increase the annealing temperature of the primer (and the Applicant specifically contemplates lengths of 1, 2, 3, 4 or 5 nucleotide residues shorter than the lengths and ranges specifically disclosed above).

The use of shorter primer and probes may be facilitated by the use of minor groove binder moieties and also lock nucleic acids (also known as locked nucleic acids or LNAs) which increase thermal stability of primers and probes and increase the annealing temperature of the primer or probe. The use of such modifications is contemplated as part of the present invention in conjunction with all of the aspects of the invention disclosed above and in particular in conjunction with probes and primers as disclosed above, but with oligomeric lengths and ranges Shortened by 5 residues from those specified above. The present invention in all its aspects contemplates use of shorter primer and probes wherein increased thermal stability is facilitated by the use of minor groove binder moieties and/or lock nucleic acids in combination with primers and probes described herein which do not have increased thermal stability as facilitated by the use of minor groove binder moieties and/or lock nucleic acids as well as exclusive use of primers and probes having increased thermal stability as facilitated by the use of minor groove binder moieties and/or lock nucleic acids.

Locked Nucleic Acids

For a recent review of lock nucleic acids, the reader is directed to Devor (2005) Integrated DNA technologies technical bulletin "Locked Nucleic Acids (LNAs)" and references therein (which are hereby incorporated by reference).

An LNA is a nucleic acid incorporating one or more modified RNA or DNA nucleotide residues (in combination with ordinary DNA or RNA residues). In the modified residue an extra covalent bridge connects the 2' and 3' carbons and "locks" the ribose sugar in the 3'—endo structural conformation as normally found in the A-form of RNA and DNA.

The term LNA includes all nucleic acids incorporating locked residues at some or all residue positions. The lock may be achieved by any chemical bridge connecting the 2' and 3' carbons of the sugar moiety. Preferably the lock is achieved in a 2'-0, 4'-C methylene linkage.

LNAs display increased thermal stability, with melting temperature rising by about 5° C. compare to corresponding DNA or RNA oligomers. Because of the elevated melting temperature, the risk of LNA primers and probes forming hairpin structures detrimental to efficient PCR reactions is increased. Good primer and probe design therefore becomes even more essential and in relation to the present application LNA primers and probes corresponding to those disclosed in SEQ ID NOS: 5, 6, 7, 11, 12 and 14, optionally shortened by 1, 2, 3, 4 or 5 residues from either end, are especially preferred.

LNAs can be readily prepared and are commercially available from a number of suppliers.

Minor Groove Binding Moieties

The invention, according to all its aspects, also relates to nucleic acid probes and primers (including LNA probes and primers) conjugated to minor groove binder (MGB) moieties.

MGB moieties are isometrical-shaped groups which bind in the minor groove of a double helix forming between the probe or primer and target. They stabilize the double stranded region and increase the melting temperature and specificity of the probe/primer, allowing shorter probes/primers to be used. For details of MGB moieties and methods of attachment the reader is referred to Katyavin et al. (2000) Nucleic Acid Res. 28(2):655-661 and references therein which are hereby incorporated by reference. Minor groove binding moieties may be readily prepared and attached to primers and probes and are commercially available from a number of suppliers.

Samples

In accordance with various aspects of the invention, samples may include clinical samples, including tissues and fluids not limited to blood, plasma, serum, secretions, semen, seminal plasma; tears and saliva. The term "sample" also includes derivatives of clinical samples, for example, samples which have been filtered, clotted, disinfected, irradiated or separated, and also used medical devices or dressings previously in contact with a subject. Said subject is preferably human.

EXAMPLES

The invention will now be illustrated with the following non-limiting examples.

a) Example 1

Selection of PCR Primers

Blastn Analysis of Chromosomal Amplicons and Primers

Blastn analysis of the 18 identified chromosomal amplicons of *Chlamydia trachomatis* was carried out. All amplicons analysed did not show any hits outside of *Chlamydia trachomatis*, with the exception of the chromosomal amplicon 18 which showed similarity to *Chlamydophila muridarum*. Primer sets did show some similarity to other species, which is expected when searching for similarity using such short sequences, however whether this is significant or not would only become apparent once exclusivity testing is carried out.

b) Example 2

Initial Testing of Primers Using Symmetric PCR

Plasmid Targets

Primer sets were obtained for plasmid amplicons 1, 3, 4, 5, 6, 7 and 8. To screen these primer sets, symmetric PCR reactions using 10,000 EBs per reaction, were set up in triplicate for each primer set according to table 1 below.

TABLE 1

Symmetric PCR reaction setup

| Reagent | Concentration | Final Concentration | Single reaction |
|---|---|---|---|
| PCR reaction buffer | 10X | 1X | 5.0 µL |

TABLE 1-continued

Symmetric PCR reaction setup

| Reagent | Concentration | Final Concentration | Single reaction |
|---|---|---|---|
| MgCl$_2$ | 25 mM | 3.0 mM | 6.0 µL |
| dUTP mix | 50.0 mM | 1.0 mM | 1.0 µL |
| Fw primer | 10 µM | 0.3 µM | 1.5 µL |
| Rv primer | 10 µM | 0.3 µM | 1.5 µL |
| (Taq) polymerase | 2.5 U/µL | 2.5 U | 1.0 µL |
| dH$_2$O | n/a | n/a | 32.0 µL |
| EBs | (5,000/µL) | 10,000 EBs | 2.0 µL |
|  |  | TOTAL | 50.0 µL |

Negative reactions were included in triplicate for each primer set. PCR reaction conditions were as follows:

1. 94° C.×1 minute
2. 94° C.×30 seconds
3. 58° C.×30 seconds
4. 72° C.×1 minutes
5. Repeat steps 2 to 4×39 cycles
6. 72° C.×3 minutes
7. 1.6° C. hold Following PCR, 10 µL of each product was run on a 2% agarose gel stained with Safeview. Following electrophoresis and visualisation of the gel using UV light, it was found that under the conditions tested, all primer sets allow amplification of the target regions, indicated by the presence of bands on the gel. Three primer sets gave the highest band intensity: plasmid amplicons 3, 5 and 7 Negative reactions showed no bands.

Chromosomal Targets

Primer sets were obtained for amplicons numbers 1, 5, 9, 17 and 18. To screen these primer sets, symmetric PCR reactions using 10,000 EBs per reaction were set up in triplicate for each primer set according to table 1 above. Negative reactions were included in triplicate for each primer set. PCR reaction conditions were as described above.

Following PCR, 10 µL of each product was run on a 2% agarose gel stained with Safeview. Following electrophoresis and visualisation of the gel using UV light, it was found that under the conditions tested, all primer sets allow amplification of the target region, indicated by the presence of bands on the gel. Chromosomal primer sets for amplicons 9 and 19 gave the highest band, intensity with the remaining sets showing slightly weaker intensities, with chromosomal amplicon 17 being marginally better than the rest.

c) Example 3

Limit of Detection (LoD) Testing Using Asymmetric PCR and Electrochemical Detection Plasmid Targets Experiments were carried out to determine the LOD of *Chlamydia trachomatis* EBs when plasmid primer sets 3, 5, 7 were used in asymmetric PCR followed by the addition of the amplicon-specific probe, digestion with T7 exonuclease and electrochemical end-point detection. Asymmetric PCR reactions using ten-fold dilutions of EBs per reaction from 100,000 to 1 were set up in triplicate for each primer set according to table 2 below.

TABLE 2 asymmetric PCR reaction setup

| Reagent | Concentration | Final Concentration | Single reaction |
|---|---|---|---|
| PCR reaction buffer | 10X | 1X | 5.0 µL |
| MgCl$_2$ | 25 mM | 3.0 mM | 6.0 µL |
| dNTP with dUTP mix | 50.0 mM | 1.0 mM | 1.0 µL |
| Fw primer | 10 µM | 0.04 µM | 0.2 µL |
| Rv primer | 10 µM | 0.3 µM | 1.5 µL |
| Taq polymerase | 2.5 U/µL | 2.5 U | 1.0 µL |
| dH$_2$O | n/a | n/a | 23.3 µL |
| EBs | Variable | Variable | 2.0 µL |
|  |  | TOTAL | 50.0 µL |

Negative reactions were included in triplicate for each primer set. PCR reaction conditions were as stated above in Example 1.

Following PCR, 20 µl of the reaction was added to 5 µl of the mastermix in table 3 below.

TABLE 3 electrochemical detection mastermix

| Reagent | Concentration | Final Concentration | Single reaction |
|---|---|---|---|
| Amplicon-specific probe | 100 µM | 3 µM | 0.75 µL |
| T7 exonuclease | 10,000 U/mL | 10 U | 1.0 µL |
| dH$_2$O | n/a | n/a | 3.25 µL |

Reactions were incubated at 37° C. for 20 minutes. Following incubation, all 25 µL was measured voltammetrically using the following Autolab parameters:

Pretreatment: Conditioning potential (V): 0, Duration: 0 s, Deposition potential: 0, Duration: 0, Equilibration time: 0, Measurement: Cell of after measurement: X, Modulation time (>=0.0025): 0.04, Interval time (>=0.105): 0.1, Potentials: Initial: −0.1, End: 0.5, Step: 0.003, Modulation amplitude: 0.04995, Standby potential (V): 0, Pretreatment: Stop equilibration at threshold: no, Equilibration Threshold value (A): 0.05, Miscellaneous: Number of scans: 1.

In each case, the peak, heights between 150-250 mV were recorded.

The electrochemical data obtained is shown in FIGS. 1a, 1b, 1c and 2c, for plasmid amplicons 3, 5 and 7, respectively. Error bars shown the SD (n=3).

Negative values obtained were "no peak" negatives. Triplicate one-copy positives were recorded for plasmid amplicons 3 and 7, however only one positive value out of three was recorded for plasmid amplicon 5. Therefore, plasmid amplicon 5 was eliminated at this stage and the experiment for plasmid amplicons 3 and 7 repeated, again in triplicate as above. These results were highly similar to that obtained above.

Although plasmid amplicon 7 showed sustained peak heights and appeared the best to use as a plasmid primer set, an exclusivity experiment using asymmetric PCR, T7 exonuclease digestion and electrochemical detection was carried out using *Chlamydophila pneumoniae*. This determined that the primer set for plasmid amplicon 7 gave a positive signal with *C. pneumoniae* (mean 88.05 nA) and as such was unsuitable for use as a *Chlamydia trachomatis*-specific primer set. Primer and probe set for plasmid amplicon 3 did not show this positive signal, and was therefore selected as the leading candidate for detection of the *Chlamydia trachomatis* plasmid.

Chromosomal Targets

Experiments were carried out to determine the LoD of *C. trachomatis* EBs when primer sets for chromosomal amplicons 9, 17 and 18 were used in asymmetric PCR followed by the addition of the appropriate amplicon-specific probe, digestion with T7 exonuclease and electrochemical endpoint detection. Asymmetric PCR reactions using ten-fold dilutions of EBs per reaction from 100,000 to 1 were set up in triplicate for each primer set according to table 2 above. Following PCR, 20 µl of the reaction was added to 5 µl of the mastermix shown in table 3 above. Reactions were incubated at 37° C. for 20 minutes. Following incubation, all 25 µl was measured voltammetrically using the parameters stated above. In each case, the peak heights between 150-250 mV were recorded.

The electrochemical data obtained is shown in FIGS. 2*a*, 2*b* and 2*c* below, for chromosomal amplicons 9, 17 and 18, respectively. Error bars shown the SD (n=3). The data-points indicate the mean of the negative values obtained.

Data obtained above would indicate that for all amplicons tested, the peak heights appear to not decrease until levels less than 1,000 EBs are used per reaction. Following this level, for chromosomal amplicons 8 and 18, peak heights decrease by about half at the 100 EB/reaction level. For chromosomal amplicon 17 this decrease is somewhat smaller. Data for chromosomal amplicon 9 shows that at a level of 10 EBs per reaction the peak heights are similar to those seen for negative samples. These data would indicate that chromosomal amplicon 17 performs better than chromosomal amplicon 18, and both of these amplicons perform better than chromosomal amplicon 9 with respect to low-end discrimination.

To improve detection at the lower end, one method that has been successfully used by the inventors is to vary the concentration of $MgCl_2$. This experiment was completed with final $MgCl_2$ concentrations per reaction of 2.0 mM to 5.0 mM in 0.5 mM increments using 10,000 EBs per asymmetric PCR, followed by probe addition, T7 digestion and electrochemical measurement. The data obtained suggested that a final $MgCl_2$ concentration of 5.0 in M allowed the greatest peak height to be obtained under the conditions tested. To confirm that this $MgCl_2$ concentration applied across all EB levels, a second LOD experiment was performed with chromosomal amplicon 17 using 5.0 mM $MgCl_2$. The results are shown in FIG. 2*d*. Error bars shown the SD (n=3). The data-points line indicates the mean of the negative values obtained.

The data shows that running PCRs using 5.0 mM $MgCl_2$ gives optimal performance when 1,000 EBs are used per reaction compared to 10,000 or 100,000 EBs per reaction. Following the 1,000 EB level, the peak heights fall to a mean value at 1 EB of 54.97 nA. Taken together, the chromosomal amplicon 17 (SEQ ID NO: 1) primer and probe set was selected as the leading candidate for *Chlamydia trachomatis* chromosomal target detection. The forward and reverse primer and probe sequences are respectively as given in SEQ ID NOS: 6, 7 and 5.

d) Example 4

Exclusivity and Inclusivity Verification

Introduction

It is essential that the *Chlamydia* assay is highly specific to *Chlamydia trachomatis* only and that no cross-reactivity is apparent across other species of bacteria or any other organisms. During the primer and probe design phase outlined in Examples 1 to 3, it was shown that bioinformatically there was no cross-reactivity, however it was essential to demonstrate this, experimentally using real microbial isolates.

Converse to this it was also essential to show that the assay was able to detect all 15 genital serovars of *Chlamydia trachomatis* and to know which other serovars (that cause ocular or arthritic disease) are also able to be amplified by the assay primer set.

DNA samples derived from a panel of bacteria were tested against both the plasmid and genomic primers to test for specificity (exclusivity) using PCR and probe-T7 endpoint detection.

To verify inclusivity, all 15 *Chlamydia trachomatis* serovars were then obtained (as EBs) and the DNA extracted, purified and quantified. Three levels of copies of DNA were then tested using both the plasmid and genomic primer sets followed by probe-T7 exonuclease endpoint detection to establish if all serovars had similar LoDs.

Exclusivity Testing

Genomic primer sets were tested in duplicate against the list of DNA as specified in the introduction. Output was measured in signal peak height following PCR, and probe-T7 detection. Testing was carried out in batches with PCR controls for each batch tested.

Chromosomal Amplicon 17 Results

Primers and probes targeting chromosomal amplicon 17 were tested against a list of genomic DNA. Results for duplicate experiments are presented below:

| Species | Peak location (milli Volts) | Peak height (nano Amps) |
|---|---|---|
| *Acinetobacter baumanii* | No peak | No peak |
| | No peak | No peak |
| *Acinetobacter* genospecies 9 | No peak | No peak |
| | No peak | No peak |
| *Acinetobacter haemolyticus* | No peak | No peak |
| | No peak | No peak |
| *Anaerococcus tetradius* | No peak | No peak |
| | No peak | No peak |
| *Arcanobacterium pyogenes* | No peak | No peak |
| | No peak | No peak |
| *Bacillus cereus* | No peak | No peak |
| | No peak | No peak |
| *Bacteroides fragilis* | No peak | No peak |
| | No peak | No peak |
| *Bacteroides thetaiotamicron* | No peak | No peak |
| | No peak | No peak |
| *Bacteroides vulgatus* | No peak | No peak |
| | No peak | No peak |
| *Bifidobacterium breve* | No peak | No peak |
| | No peak | No peak |
| *Bordetella pertussis* | No peak | No peak |
| | No peak | No peak |
| *Burkholderia cepacia* | No peak | No peak |
| | No peak | No peak |
| *Citrobacter diversus* | No peak | No peak |
| | No peak | No peak |
| *Citrobacter freundii* | No peak | No peak |
| | No peak | No peak |

| Species | Peak location (milli Volts) | Peak height (nano Amps) |
|---|---|---|
| Clostridium difficile | No peak | No peak |
| | No peak | No peak |
| Corynebacterium urealyticum | No peak | No peak |
| | No peak | No peak |
| Enterobacter aerogenes | No peak | No peak |
| | No peak | No peak |
| Enterococcus casseliflavus | No peak | No peak |
| | No peak | No peak |
| Enterococcus dispar | No peak | No peak |
| | No peak | No peak |
| Enterococcus gallinarum | No peak | No peak |
| | No peak | No peak |
| Enterococcus mundtii | No peak | No peak |
| | No peak | No peak |
| Enterococcus raffinosus | No peak | No peak |
| | No peak | No peak |
| Escherichia hermanii | No peak | No peak |
| | No peak | No peak |
| Finegoldia magna | No peak | No peak |
| | No peak | No peak |
| Gardnerella vaginalis | No peak | No peak |
| | No peak | No peak |
| Haemophilus influenzae | No peak | No peak |
| | No peak | No peak |
| Hafnia alvei | No peak | No peak |
| | No peak | No peak |
| Klebsiella oxytoca | No peak | No peak |
| | No peak | No peak |
| Lactobacillus casei | No peak | No peak |
| | No peak | No peak |
| Lactobacillus crispatus | No peak | No peak |
| | No peak | No peak |
| Lactobacillus gasseri | No peak | No peak |
| | No peak | No peak |
| Lactobacillus reuteri | No peak | No peak |
| | No peak | No peak |
| Listeria innocua | No peak | No peak |
| | No peak | No peak |
| Mobiluncus curtisii subsp. Holmesii | No peak | No peak |
| | No peak | No peak |
| Mobiluncus mulieris | No peak | No peak |
| | No peak | No peak |
| Moraxella catarrhalis | No peak | No peak |
| | No peak | No peak |
| Morganella morganii subsp. Morganii | No peak | No peak |
| | No peak | No peak |
| Moraxella osloensis | No peak | No peak |
| | No peak | No peak |
| Pantoea agglomerans | No peak | No peak |
| | No peak | No peak |
| Peptostreptococcus anaerobius | No peak | No peak |
| | No peak | No peak |
| Prevotella bivia | No peak | No peak |
| | No peak | No peak |
| Propionibacterium acnes | No peak | No peak |
| | No peak | No peak |
| Proteus rettgeri | No peak | No peak |
| | No peak | No peak |
| Serratia marcescens subsp. marcescens | 196 | 30 |
| | 205 | 20 |
| Shigella flexneri | No peak | No peak |
| | No peak | No peak |
| Shigella sonnei | No peak | No peak |
| | No peak | No peak |
| Staphylococcus capitis subsp. capitis | No peak | No peak |
| | No peak | No peak |
| Staphylococcus haemolyticus | No peak | No peak |
| | No peak | No peak |
| Staphylococcus hominis subsp. hominis | No peak | No peak |
| | 205 | 17.7 |
| Staphylococcus intermedius | 193 | 19.6 |
| | No peak | No peak |
| Staphyococcus saprophyticus subsp. saprophyticus | No peak | No peak |
| | No peak | No peak |
| Stenotrophomonas maltophilia | No peak | No peak |
| | No peak | No peak |
| Streptococcus anginosus | No peak | No peak |
| | No peak | No peak |
| Streptococcus australis | No peak | No peak |
| | No peak | No peak |
| Streptococcus bovis | No peak | No peak |
| | No peak | No peak |
| Streptococcus constellatus subsp. constellatus | No peak | No peak |
| | No peak | No peak |
| Streptococcus equinus | No peak | No peak |
| | No peak | No peak |
| Streptococcus gordonii | No peak | No peak |
| | No peak | No peak |
| Streptococcus mitis | No peak | No peak |
| | No peak | No peak |
| Streptococcus mutans | No peak | No peak |
| | No peak | No peak |
| Streptococcus oralis | No peak | No peak |
| | No peak | No peak |
| Streptococcus porcinus | No peak | No peak |
| | No peak | No peak |
| Streptococcus suis | No peak | No peak |
| | No peak | No peak |
| Streptococcus uberis | No peak | No peak |
| | No peak | No peak |
| Yersinia enterocolitica subsp. enterocolitica | 199 | 14.5 |
| | No peak | No peak |
| Streptococcus pyogenes | No peak | No peak |
| | 208 | 14.3 |
| Enterobacter cloacae | No peak | No peak |
| | No peak | No peak |
| Lactococcus lactis | No peak | No peak |
| | 199 | 16.6 |
| Clostridium perfringens | No Peak | No Peak |
| | 199 | 12.2 |
| Klebsiella pneumoniae | No peak | No peak |
| | No peak | No peak |
| Pseudomonas aeruginosa | No peak | No peak |
| | No peak | No peak |
| Escherichia coli | No peak | No peak |
| | No peak | No peak |
| Proteus vulgaris | No peak | No peak |
| | No peak | No peak |
| Campylobacter coli | No peak | No peak |
| | No peak | No peak |
| Staphylococcus aureus | No peak | No peak |
| | No peak | No peak |
| Streptococcus pneumoniae | No peak | No peak |
| | No peak | No peak |
| Streptococcus dysgalactiae | No peak | No peak |
| | No peak | No peak |
| Homo sapiens | No peak | No peak |
| | No peak | No peak |
| Neiserria gonorrhoeae | No peak | No peak |
| | No peak | No peak |
| Candida albicans | No peak | No peak |
| | No peak | No peak |
| Streptococcus agalactiae | No peak | No peak |
| | 202 | 6.24 |
| Pectobacterim atrosepticum | No peak | No peak |
| | No peak | No peak |
| Chlamydia pecorum | No peak | No peak |
| | No peak | No peak |
| Chlamydia psittaci | No peak | No peak |
| | No peak | No peak |
| PCR positive | 205 | 96.8 |
| | 193 | 73.5 |
| PCR negative | No peak | No peak |
| | No peak | No peak |

Overall Conclusions—Exclusivity

Both primer sets showed no cross-reactivity indicating that the *Chlamydia* assay is highly specific.

Inclusivity Testing

EBs obtained for all 15 *C. trachomatis* serotypes (A, B, Ba, C, D, E, F, G, H, I, J, K, L1, L2, L3) were lysed and their DNA purified and quantified. Levels of 50,000, 500, 50 or 5 genome copies of each serotype were tested for inclusivity in PCR reactions using primers and probes as outlined above (SEQ ID NOS: 6 and 7 and 5). Signal peak height was measured after endpoint detection using probe-T7.

Chromosomal Amplicon 17 Inclusivity Results

| Serotype | EB level/PCR | Peak Position (mV) | Peak Height (nA) |
|---|---|---|---|
| A | 50,000 | 193 | 177 |
|  | 50,000 | 187 | 184 |
|  | 500 | 193 | 120 |
|  | 50 | 193 | 91.3 |
|  | 5 | 193 | 19.8 |
|  | 5 | 193 | 43.2 |
| B | 50,000 | 190 | 217 |
|  | 50,000 | 193 | 188 |
|  | 500 | 190 | 115 |
|  | 50 | 190 | 128 |
|  | 5 | 196 | 15.7 |
|  | 5 | 190 | 35.4 |
| C | 50,000 | 193 | 184 |
|  | 50,000 | 193 | 198 |
|  | 500 | 190 | 125 |
|  | 50 | 190 | 93.8 |
|  | 5 | 196 | 49.8 |
|  | 5 | 202 | 45 |
| D | 50,000 | 193 | 146 |
|  | 50,000 | 190 | 135 |
|  | 500 | NP | NP |
|  | 50 | 196 | 36.4 |
|  | 5 | NP | NP |
|  | 5 | NP | NP |
| E | 50,000 | 193 | 201 |
|  | 50,000 | 193 | 151 |
|  | 500 | 193 | 72.4 |
|  | 50 | 193 | 79.3 |
|  | 5 | NP | NP |
|  | 5 | 199 | 14.2 |
| F | 50,000 | 193 | 204 |
|  | 50,000 | 190 | 179 |
|  | 500 | 196 | 126 |
|  | 50 | 199 | 149 |
|  | 5 | 202 | 36.8 |
|  | 5 | NP | NP |
| G | 50,000 | 193 | 91.1 |
|  | 50,000 | 196 | 80.5 |
|  | 500 | 202 | 38.9 |
|  | 500 | 199 | 42.1 |
|  | 5 | NP | NP |
|  | 5 | 202 | 10.2 |
| H | 50,000 | 196 | 200 |
|  | 50,000 | 202 | 246 |
|  | 500 | 193 | 64.3 |
|  | 50 | 205 | 97.5 |
|  | 5 | 196 | 14.3 |
|  | 5 | 205 | 17.6 |
| I | 50,000 | 190 | 166 |
|  | 50,000 | 190 | 204 |
|  | 500 | 193 | 114 |
|  | 50 | 190 | 107 |
|  | 5 | 196 | 16.5 |
|  | 5 | 196 | 42.3 |
| J | 50,000 | 208 | 181 |
|  | 50,000 | 193 | 144 |
|  | 500 | 196 | 52.1 |
|  | 50 | 193 | 49.2 |
|  | 5 | NP | NP |
|  | 5 | NP | NP |
| K | 50,000 | 193 | 181 |
|  | 50,000 | 190 | 204 |
|  | 500 | 211 | 111 |
|  | 50 | 193 | 73.5 |
|  | 5 | NP | NP |
|  | 5 | NP | NP |
| L1 | 50,000 | 199 | 188 |
|  | 50,000 | 196 | 247 |
|  | 500 | NP | NP |
|  | 50 | 199 | 147 |
|  | 5 | 193 | 191 |
|  | 5 | 196 | 32.7 |
| L2 | 50,000 | 196 | 200 |
|  | 50,000 | 214 | 403 |
|  | 500 | 196 | 135 |
|  | 50 | 199 | 123 |
|  | 5 | 199 | 62.5 |
|  | 5 | 199 | 68.6 |
| L3 | 50,000 | 196 | 258 |
|  | 50,000 | 199 | 247 |
|  | 500 | 193 | 171 |
|  | 50 | 193 | 122 |
|  | 5 | 199 | 34.3 |
|  | 5 | 202 | 15.4 |
| PCR controls | Positive | 193 | 146 |
|  | Positive | 193 | 147 |
|  | Negative | NP | NP |
|  | Negative | NP | NP |

Overall Conclusion—Inclusivity

Using the primer (SEQ ID NO: 6 and SEQ ID NO: 7) and probe (SEQ ID NO: 5) set for genomic amplicon 17 all serotypes are able to be amplified and electrochemically detected at 5 copies except for serotypes D, J and K. These were reported, along with serotype G using the primer and probe set for genomic amplicon 17 and showed D was able to be amplified at 50 copies, J at 50 copies and K at 50 copies.

e) Example 5

Identification and Uniqueness of *Pectobacterium Atrospeticum* Target Genes for Use as an Internal Control The 5.064 Mb *Pectobacterium atrospeticum* genome (accession No. BX950851) was downloaded from the NCBI Pubmed website. The *Pectobacterium atrosepticum* genome is fully annotated with gene names, functions and genomic location, including hypothetical genes. Three genes were selected for investigation.

These were rfaH, (starting at base pair position 230144 of 489 bp in length running in the reverse orientation which encodes a transcriptional activator protein), mgsA, (starting at base pair position 2008746 of 458 bp in length running in the reverse orientation which encodes a methylgloxal synthase) and a gene encoding a hypothetical protein, designated HP1, starting at base pair position 143610 of 387 bp in length running in the reverse orientation. Interrogation of these genes using the NCBI's Blastn program with filters set to the full nucleotide collection determined that the only hits found were in *Pectobacterium atrosepticum* itself, meaning that primers designed to amplify regions of these genes should not amplify regions from other genera, not limited to bacteria.

Primer/Probe Design

The full-length gene sequences were selected from the genome using the Clone Manager program. The primer design function of the program was used to choose primer sets of optimal length 20 bases (18-22 bases acceptable), amplifying a product of between 90 and 150 bp from each gene. The criteria applied for each primer were to have a GC % of between 50-60%, a Tm of 50-80° C., with less than 3 matches at the 3' end, less than 7 adjacent homologous bases, stability greater than or equal to 1.2 kcal at the 5' end vs the 3' end, at least one G or C at the 3' end, less than four base runs, less than three dinucleotide repeats and no hairpins with annealing temperatures of 55° C. Based on these criteria, three primer sets were found, amplifying 124 bp from rfaH, 91 bp from mgsA and 98 bp from HP1. Single stranded DNA probes were designed using the Clone Manager program using the following criteria: GC % of 50-60%, Tm of 32-100° C., less than 5 adjacent homologous bases, less than 4 base runs, less than 3 dinucleotide repeats and no hairpins at an annealing temperature of 42° C.

Primer/Probe Testing

Initial Amplification of Target Sequences

The three primer sets were tested using PCR with *Pectobacterium atrospeticum* strain SCRI1043 genomic DNA corresponding to ATCC bacterial deposit having accession number BAA-672. Symmetric PCR was carried out using the reaction conditions shown in the table below and cycling conditions as shown in table 4 and table 5 below.

TABLE 4

PCR reaction conditions for symmetric testing

| | Volume/reaction, µl |
|---|---|
| 10x PCR buffer | 3 |
| MgCl$_2$, 25 mM | 1.8 |
| dNTPs, 6 mM | 3 |
| Primer forward, 10 µM | 1.5 |
| Primer reverse, 10 µM | 1.5 |
| Taq pol. 5 U/µl | 0.3 |
| (DNA, 2 ng/µl) | 2 |
| dH2O | 16.9 |
| TOTAL | 30 |

TABLE 5

PCR cycling conditions

| Cycle Step | Temperature | Duration |
|---|---|---|
| 1 | 94° C. | 1 min |
| 2 | 94° C. | 20 s |
| 3 | 58° C. | 20 s |
| 4 | 72° C. | 20 s |
| 5 | Go to 2, 39 cycles | |
| 6 | 72° C. | 3 min |
| 7 | 16° C. | Hold |

Following thermocycling, 10 µl of amplified PCR product was run on a 1.5% agarose gel. Following electrophoresis, the gel was photographed under UV light. Using a 100 bp DNA ladder as a reference, all primer sets amplified the desired products under these conditions. Limit of detection experiments carried out in triplicate, using various amounts of *Pectobacterium atrospeticum* genomic DNA under identical PCR reaction and cycling conditions determined that rfaH was amplified at all levels tested from 2 ng (366,468 copies) down to a total DNA amount of 2 pg (366 genome copies), whereas mgsA and HP1 were detected at all levels from 2 ng down to 200 fg (37 genome copies). Negative controls were included as appropriate.

f) Example 6

Symmetric and Asymmetric, Amplification and Detection Using Electrochemical Probes Electrochemical probes were synthesised using ferrocene labels for each of the three probe sequences. Two nanograms of *Pectobacterium atrospeticum* genomic DNA was amplified in triplicate reactions using the rfaH, mgsA and HP 1 primer sets under symmetric PCR conditions (shown in table 5, above) or asymmetric PCR conditions using the reaction conditions shown in table 6 (below), both with the cycling conditions shown in table 5 above. Triplicate negative (water-only) controls were run in triplicate for each primer set for each amplification condition.

TABLE 6

PCR reaction conditions for asymmetric testing

| | Volume/reaction, µl |
|---|---|
| 10x PCR buffer | 3 |
| MgCl$_2$, 25 mM | 1.8 |
| dNTPs, 6 mM | 3 |
| Primer, 10 µM in excess* | 1.5 |
| Primer, 10 µM not in excess* | 0.2 |
| Taq pol. 5 U/µl | 0.3 |
| (DNA, 2 ng/µl) | 2 |
| dH$_2$0 | 18.2 |
| TOTAL | 30 |

*Primers in excess were rfaH reverse, mgsA forward and HP1 reverse.

For symmetric PCR only, 10 µl of each reaction volume was run on a 1.5% agarose gel to visualise PCR product sizes. This confirmed the presence of PCR product.

An appropriate mastermix was made for each amplicon-specific 14-151 probes as shown in table 7 below.

TABLE 7

Mastermix for electrochemical detection

| Reagent | Concentration | Final Concentration | Single reaction |
|---|---|---|---|
| Amplicon-specific probe | 100 µM | 3 µM | 0.75 µL |
| T7 exonuclease | 10,000 U/mL | 10 U | 1.0 µL |
| dH$_2$O | n/a | n/a | 3.25 µL |

Five microlitres of the appropriate probe mix were added to 20 µl of PCR product and the mixture was incubated at 37° C. for 20 minutes. Following incubation, the electrochemical potential was measured electrochemically using the following Autolab parameters:

Pretreatment: Conditioning potential (V): 0, Duration: 0 s, Deposition potential: 0, Duration: 0, Equilibration time: 0, Measurement: Cell of after measurement: X, Modulation time (>=0.0025): 0.04, Interval time (>=0.105): 0.1, Potentials: Initial: −0.1, End: 0.5, Step: 0.003, Modulation amplitude: 0.04995, Standby potential (V): 0, Pretreatment: Stop equilibration at threshold: no, Equilibration threshold value (A): 0.05, Miscellaneous: Number of scans: 1.

The mean (n=3) data obtained from the electrochemical readings is shown in table 8 below.

TABLE 8

Summary of electrochemical data obtained for each amplicon/probe set

| Amplicon | Conditions | Type | Peak Location, mV | Peak Height, nA Mean | SD | CV |
|---|---|---|---|---|---|---|
| rfaH | Asymmetric | Positive | 194 | 280.67 | 19.6 | 6.98 |
|  | Asymmetric | Negative | 180 | 39.93 | 1.85 | 4.63 |
| mgsA | Asymmetric | Positive | 189 | 206.33 | 49.2 | 23.85 |
|  | Asymmetric | Negative | 187 | 25.77 | 2.47 | 9.58 |
| HP1 | Asymmetric | Positive | 190 | 611.33 | 15.37 | 2.51 |
|  | Asymmetric | Negative | 177 | 53.7 | 5.29 | 9.85 |

The data shown in Table 8 clearly indicate that the peak heights obtained using the HP1 probe was higher than all others tested with mean peak heights of 611.33 nA being obtained. Along with mean negative peak heights of 53.7, this would allow the greatest possible discrimination between positive and negative signals. The peak locations for asymmetric conditions for positive HP1 samples were identical, and asymmetric conditions for negative HP1 samples gave low standard deviation and coefficient of variation. The mgsA amplicon/probe set allowed poor discrimination and the rfaH ampicon/probe set gave good discrimination, however this was not of the order seen with the HP1 set. Therefore, the HP1 primer/probe set was chosen for internal control purposes. The chosen forward primer corresponds to SEQ ID NO: 11. The chosen reverse primer corresponds to SEQ ID NO: 12. The chosen probe corresponds to SEQ ID NO: 14.

d) Example 7

Exclusivity Verification for Internal Control Probe and Primer Set

Introduction

It is essential that the internal control assay highly specific and that no cross-reactivity is apparent across other DNA which may be present in a patient sample (for example, human DNA and for nucleic acid from infectious organisms.

DNA samples derived from a panel of bacteria were tested against the internal control primers (SEQ ID NOS: 11 and 12) to test for specificity (exclusivity) using PCR and probe-T7 exonuclease endpoint detection, with probe sequence as in SEQ ID NO: 14.

Genomic primer sets were tested in duplicate against the list of DNA as specified in the results. Output was measured in signal peak height following PCR, and probe-T7 exonuclease detection. Testing was carried out in batches with PCR controls for each batch tested.

Internal Control Results

Primers and probes targeting *Pectobacterium atrosepticium* were tested against a list of genomic DNA. Results for duplicate experiments are presented below:

| Species | Peak location (milli Volts) | Peak height (nano Amps) |
|---|---|---|
| *Acinetobacter baumanii* | No peak | No peak |
|  | No peak | No peak |
| *Acinetobacter* genospecies 9 | No peak | No peak |
|  | No peak | No peak |
| *Acinetobacter haemolyticus* | No peak | No peak |
|  | 202 | 26.0 |
| *Anaerococcus tetradius* | No peak | No peak |
|  | No peak | No peak |
| *Arcanobacterium pyogenes* | No peak | No peak |
|  | 202 | 30.2 |
| *Bacillus cereus* | 202 | 20.3 |
|  | No peak | No peak |
| *Bacteroides fragilis* | No peak | No peak |
|  | No peak | No peak |
| *Bacteroides thetaiotamicron* | No peak | No peak |
|  | 202 | 35.3 |
| *Bacteroides vulgatus* | No peak | No peak |
|  | No peak | No peak |
| *Bifidobacterium breve* | 193 | 16.8 |
|  | No peak | No peak |
| *Bordetella pertussis* | No peak | No peak |
|  | No peak | No peak |
| *Burkholderia cepacia* | No peak | No peak |
|  | No peak | No peak |
| *Citrobacter diversus* | 205 | 19.8 |
|  | No peak | No peak |
| *Citrobacter freundii* | No peak | No peak |
|  | No peak | No peak |
| *Clostridium difficile* | No peak | No peak |
|  | No peak | No peak |
| *Corynebacterium urealyticum* | No peak | No peak |
|  | No peak | No peak |
| *Enterobacter aerogenes* | No peak | No peak |
|  | No peak | No peak |
| *Enterococcus casseliflavus* | No peak | No peak |
|  | No peak | No peak |
| *Enterococcus dispar* | No peak | No peak |
|  | No peak | No peak |
| *Enterococcus gallinarum* | No peak | No peak |
|  | No peak | No peak |
| *Enterococcus mundtii* | No peak | No peak |
|  | No peak | No peak |
| *Enterococcus raffinosus* | No peak | No peak |
|  | No peak | No peak |
| *Escherichia hermanii* | No peak | No peak |
|  | No peak | No peak |
| *Finegoldia magna* | No peak | No peak |
|  | No peak | No peak |
| *Gardnerella vaginalis* | 211 | 46.0 |
|  | No peak | No peak |
| *Haemophilus influenzae* | No peak | No peak |
|  | No peak | No peak |
| *Hafnia alvei* | No peak | No peak |
|  | No peak | No peak |
| *Klebsiella oxytoca* | No peak | No peak |
|  | No peak | No peak |
| *Lactobacillus casei* | No peak | No peak |
|  | No peak | No peak |
| *Lactobacillus crispatus* | No peak | No peak |
|  | No peak | No peak |
| *Lactobacillus gasseri* | No peak | No peak |
|  | 211 | 31.4 |
| *Lactobacillus reuteri* | No peak | No peak |
|  | No peak | No peak |
| *Listeria innocua* | No peak | No peak |
|  | 211 | 36.0 |
| *Mobiluncus curtisii* subsp. *Holmesii* | No peak | No peak |
|  | No peak | No peak |
| *Mobiluncus mulieris* | No peak | No peak |
|  | No peak | No peak |
| *Moraxella catarrhalis* | No peak | No peak |
|  | No peak | No peak |
| *Morganella morganii* subsp. *Morganii* | No peak | No peak |
|  | No peak | No peak |
| *Moraxella osloensis* | No peak | No peak |
|  | No peak | No peak |
| *Pantoea agglomerans* | No peak | No peak |
|  | No peak | No peak |
| *Peptostreptococcus anaerobius* | No peak | No peak |
|  | No peak | No peak |
| *Prevotella bivia* | No peak | No peak |
|  | No peak | No peak |

-continued

| Species | Peak location (milli Volts) | Peak height (nano Amps) |
|---|---|---|
| Propionibacterium acnes | No peak | No peak |
| | No peak | No peak |
| Proteus rettgeri | No peak | No peak |
| | No peak | No peak |
| Serratia marcescens subsp. marcescens | No peak | No peak |
| | No peak | No peak |
| Shigella flexneri | No peak | No peak |
| | No peak | No peak |
| Shigella sonnei | No peak | No peak |
| | No peak | No peak |
| Staphylococcus capitis subsp. capitis | No peak | No peak |
| Staphylococcus haemolyticus | No peak | No peak |
| | No peak | No peak |
| Staphylococcus hominis subsp. hominis | No peak | No peak |
| Staphylococcus intermedius | No peak | No peak |
| | No peak | No peak |
| Staphyococcus saprophyticus subsp. saprophyticus | No peak | No peak |
| Stenotrophomonas maltophilia | No peak | No peak |
| Streptococcus anginosus | No peak | No peak |
| | No peak | No peak |
| Streptococcus australis | No peak | No peak |
| | No peak | No peak |
| Streptococcus bovis | No peak | No peak |
| | No peak | No peak |
| Streptococcus constellatus subsp. constellatus | 214 | 37.9 |
| Streptococcus equinus | No peak | No peak |
| | No peak | No peak |
| Streptococcus gordonii | No peak | No peak |
| | No peak | No peak |
| Streptococcus mitis | No peak | No peak |
| | No peak | No peak |
| Streptococcus mutans | No peak | No peak |
| | No peak | No peak |
| Streptococcus oralis | No peak | No peak |
| | No peak | No peak |
| Streptococcus porcinus | No peak | No peak |
| | 217 | 39.8 |
| Streptococcus suis | No peak | No peak |
| | No peak | No peak |
| Streptococcus uberis | No peak | No peak |
| | No peak | No peak |
| Yersinia enterocolitica subsp. enterocolitica | No peak | No peak |
| Streptococcus pyogenes | No peak | No peak |
| | No peak | No peak |
| Enterobacter cloacae | No peak | No peak |
| | No peak | No peak |
| Lactococcus lactis | No peak | No peak |
| | No peak | No peak |
| Clostridium perfringens | No peak | No peak |
| | No peak | No peak |
| Klebsiella pneumoniae | No peak | No peak |
| | No peak | No peak |
| Pseudomonas aeruginosa | No peak | No peak |
| | No peak | No peak |
| Escherichia coli | No peak | No peak |
| | No peak | No peak |
| Proteus vulgaris | No peak | No peak |
| | No peak | No peak |
| Campylobacter coli | No peak | No peak |
| | 245 | 24.3 |
| Staphylococcus aureus | 224 | 39.2 |
| | No peak | No peak |
| Streptococcus pneumoniae | No peak | No peak |
| | No peak | No peak |
| Streptococcus dysgalactiae | No peak | No peak |
| | No peak | No peak |
| Homo sapiens | 199 | 19.6 |
| | No peak | No peak |
| Neisserria gonorrhoeae | No peak | No peak |
| | No peak | No peak |

-continued

| Species | Peak location (milli Volts) | Peak height (nano Amps) |
|---|---|---|
| Candida albicans | No peak | No peak |
| | No peak | No peak |
| Streptococcus agalactiae | 236 | 17.9 |
| | 220 | 41.9 |
| Trichomonas vaginalis | No peak | No peak |
| | No peak | No peak |
| Mycoplasma genitalium | 208 | 10.9 |
| | No peak | No peak |
| Chlamydia trachomatis | 211 | 37.1 |
| | 208 | 18.1 |
| Enterococcus faecalis | 202 | 28.6 |
| | No peak | No peak |
| Chlamydia pecorum | No peak | No peak |
| | No peak | No peak |
| Chlamydia psittaci | No peak | No peak |
| | No peak | No peak |
| Candida glabrata | No peak | No peak |
| | No peak | No peak |
| PCR positive | 196.00 | 251.0 |
| | 196 | 277.0 |
| PCR negative | No peak | No peak |
| | 202 | 29.2 |

Example 8

Further Test of Chromosomal Amplicon 17 Primer and Probe Set Against *Chlamydia Trachomatis*

A PCR mastermix was made by combining the following:

| Material | Volume (µL) |
|---|---|
| 10x PCR Buffer | 2.5 |
| MgCl$_2$ (25 mM) | 5.0 |
| dUTP mix | 0.5 |
| ME17 F primer (SEQ ID NO: 6) | 0.1 |
| ME17 R primer (SEQ ID NO: 7) | 0.75 |
| UDG | 0.25 |
| Taq Polymerase | 0.25 |
| Mol Biol. Grade H$_2$O | 3.15 |

The mastermix was divided into aliquots of 12.5 µl. DNA extracted from 1,000, 100, 10 and 0 *C. trachomatis* EBs was added in 12.5 µl volumes. Samples were then incubated for UDG activity and denaturation followed by PCR as described below:

| Step | Temperature (° C.) | Duration |
|---|---|---|
| 1 | 37 | 10 min |
| 2 | 94 | 10 min |
| 3 | 94 | 30 sec |
| 4 | 58 | 45 sec |
| 5 | 72 | 60 sec |
| 6 | Go to step 3 39 times | |
| 7 | 72 | 7 min |

Amplified samples were used as a target for detection in the following assay using 0.8 U T7 exonuclease and 9 µM specific probe having the sequence of SEQ ID NO: 5 (final reaction concentrations). Each sample was assayed in triplicate.

The detection mix was made up by combining:

| Material | 1x | 30x |
| --- | --- | --- |
| ME17 probe | 1.125 | 33.75 |
| T7 exonuclease | 0.2 | 6.0 |

1.325 µl of each detection mix was added to 11.175 µl of each amplification sample in triplicate and placed at 37° C. for 20 minutes before voltammetric analysis on fresh electrodes using the following Autolab parameters:
  Pretreatment: Conditioning potential (V): 0, Duration: 0 s, Deposition potential: 0, Duration: 0, Equilibration time: 0,
  Measurement: Cell of after measurement: X, Modulation time (>=0.0025): 0.04, Interval time (>=0.105): 0.1,
  Potentials: Initial: −0.1, End: 0.5, Step: 0.003, Modulation amplitude: 0.04995, Standby potential (V): 0,
  Pretreatment: Stop equilibration at threshold: no, Equilibration threshold value (A): 0.05,
  Miscellaneous: Number of scans: 1.

The peak height and exact peak position for the peak, located at approximately 150-200 mV was recorded.

Results are shown in FIG. 3.

Whilst the data presented in the above examples provides evidence for the disclosed primers, probes and methods being advantageous when employed in "singlex" reactions because the above experiments did not involve trials of duplex PCRs wherein *Chlamydia trachomatis* and the internal control reactions were run together and each probed in order to detect both targets in a single tube, the following further examples were carried out.

Example 9

Duplex Trial 1

Method Summary

Both optimized "singlex" reactions detailed above were repeated but with the addition of the primer set specific for the second analyte along with the target analyte DNA.

Results

It was found that something in the duplex reaction mix was reducing the electrochemical peak heights for the *Chlamydia* target. This effect can be seen in FIG. 4 in an experiment where the ME17 *Chlamydia* chromosomal primer set was run in the presence and absence of the Internal Control primer set, both with and without 200 pg Internal Control DNA. FIG. 4 clearly shows that the amplification of *C. trachomatis* in the presence of the Internal Control primer set, and not Internal Control DNA alone, adversely affects the electrochemical signal obtained for detections using the *C. trachomatis* probe. The same experiment was carried out using the Internal Control probe to electrochemically detect internal control amplicons. The data obtained is shown in FIG. 5.

Figure 5:
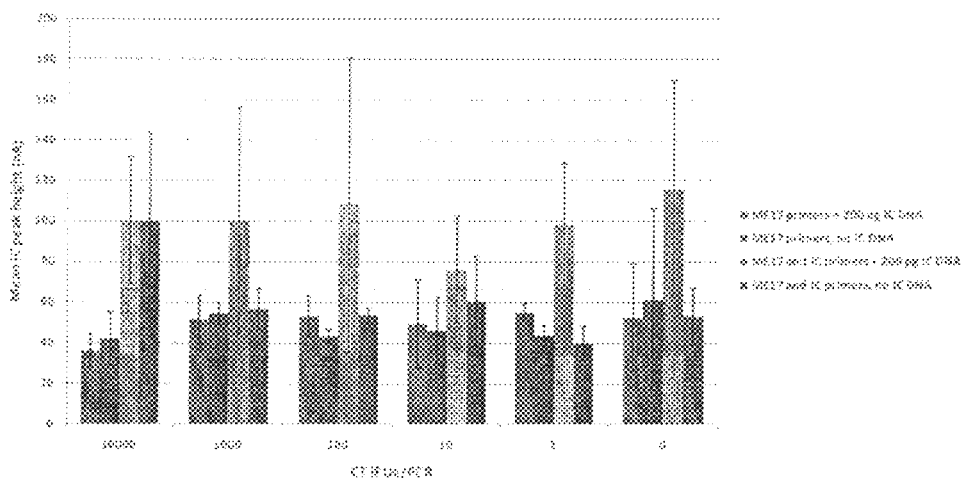
Figure 6A:
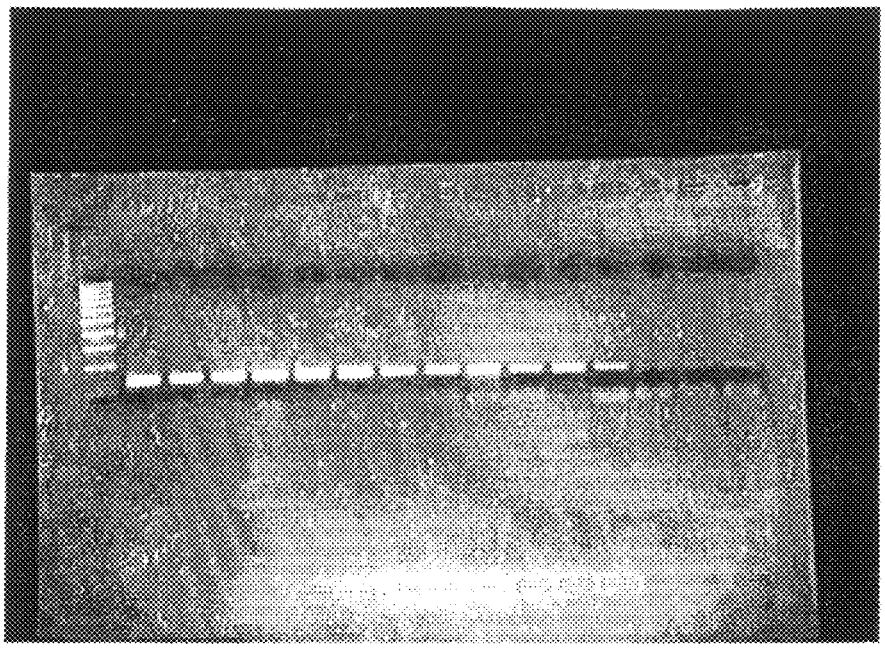
Figure 6B:
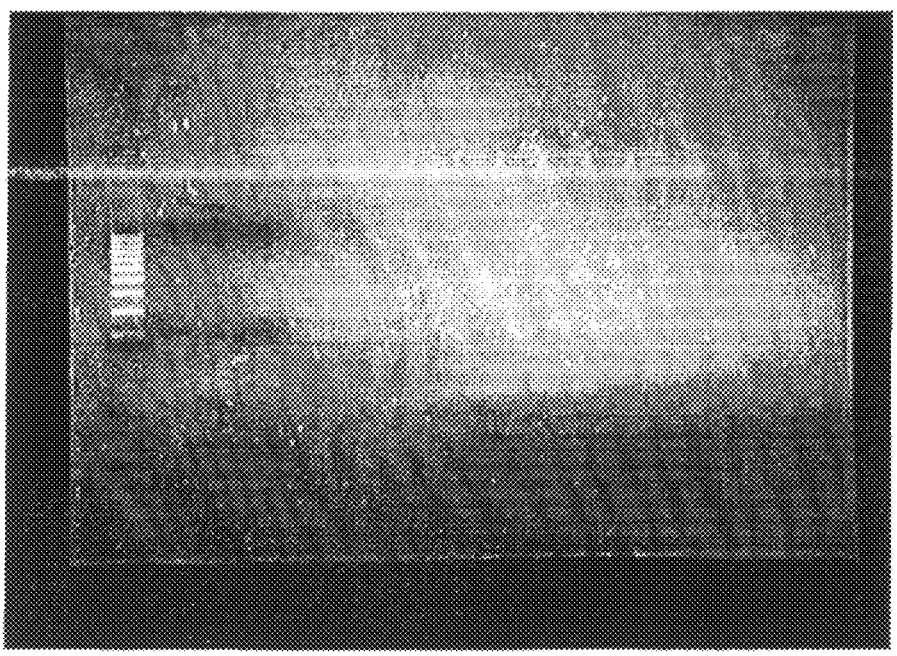
Figure 7A:
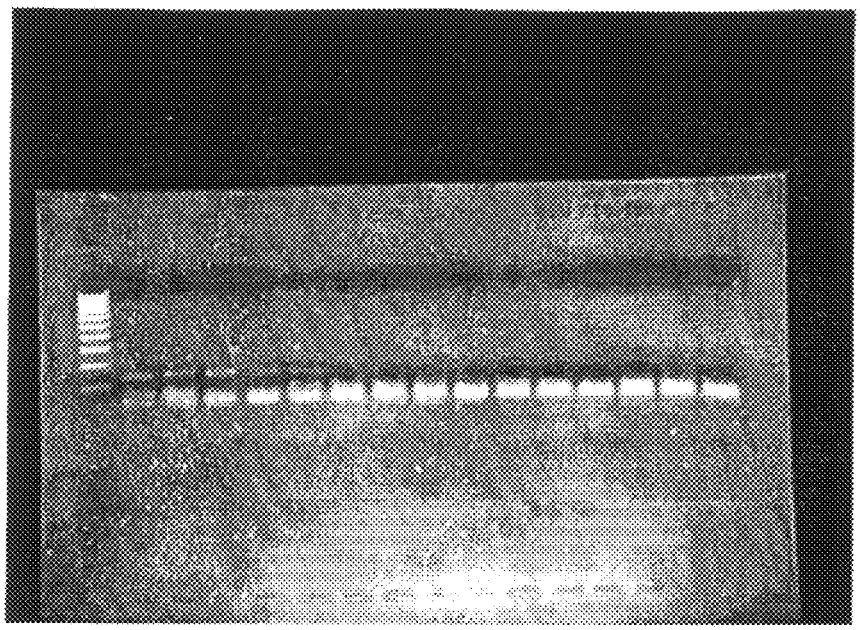
Figure 7B:
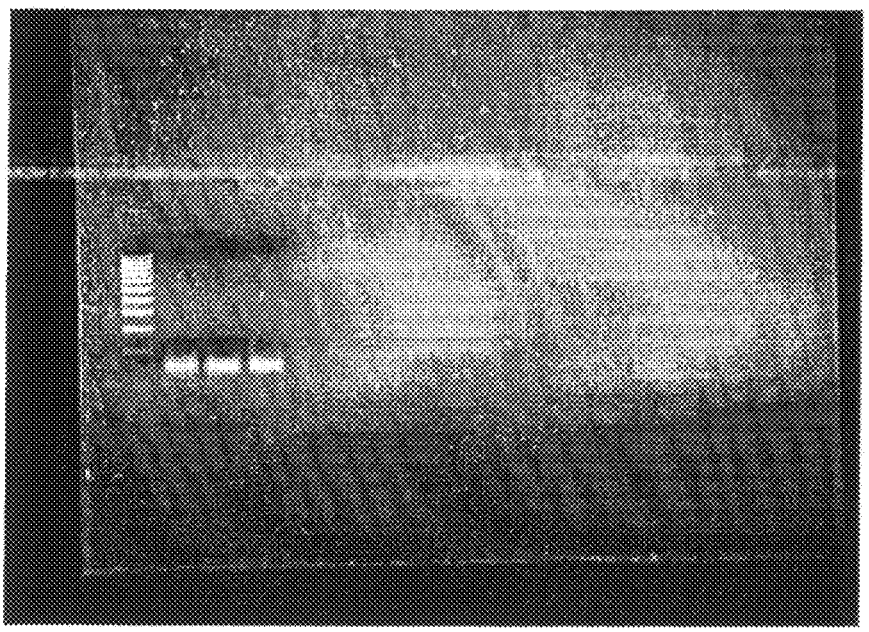

FIG. 5 shows a dramatic reduction in the Internal Control electrochemical signal expected for "singlex" PCRs containing the Internal Control Primers and 200 pg chromosomal Internal Control target molecule, where peak heights in excess of 1,000 nA are commonly observed. These data were curious, given that in other duplex assays no interference is observed between the target chromosomal DNA and the Internal Control. Taken together, these data pointed to either the *C. trachomatis* or Internal Control primer sets not functioning in a *C. trachomatis*/Internal Control duplex assay. These data were confirmed by carrying out an experiment using symmetric PCR to amplify. *C. trachomatis*, with and without the Internal Control primer set, using agarose gel electrophoresis as a detection method. The gel photographs are shown below in FIGS. 6a and 6b (*C. trachomatis* primer sets alone) and FIGS. 7a and 7b (*C. trachomatis* and Internal Control primer sets).

When the Internal Control primer set is included in an otherwise identical PCR reaction, detection is only possible down to the 1,000 IFU/reaction level, showing that the Internal Control primer set reduces the amplification efficiency of *C. trachomatis* IFUs by three logs (as determined by gel electrophoresis).

A further symmetric PCR experiment, with amplicons detected using agarose gel electrophoresis was conducted to refine the above to determine which of the Internal Control Primers was interfering with the detection of *C. trachomatis*. This experiment showed that when *C. trachomatis* was amplified in the presence of the Internal Control forward primer, an amplified product of correct molecular weight was observed down to the 10 *C. trachomatis* IFU/reaction level. However, when the Internal Control reverse primer was included in a *C. trachomatis* amplification, the limit of detection of the *C. trachomatis* amplification was increased to 10,000 IFU/reaction. The gel photograph also suggested that a strong primer dimer was forming under PCR conditions using the *C. trachomatis* primer set in combination with the Internal Control reverse primer, as indicated by a thick low molecular weight band on the gel.

Bioinformatic analyses of the Internal Control reverse primer and the *C. trachomatis* forward and reverse primers showed that the five terminal bases of the 3' ends of both the Internal Control forward primer and *C. trachomatis* reverse primer were complementary, accounting for the primer dimmers observed on the agarose gel, and also the poor performance in duplex amplifications. The sequence similarity is shown below.

```
                                            [SEQ ID NO: 7]
    5'-TTCCAGAGGCAATGCCAAAG-3'-C. trachomatis rv
           :::::                    [SEQ ID NO: 12]
          3'-GTTTCCTAAGGGTCAAGTCa-5'-IC fw
```

The sequence similarity is hypothesized to account for the poor amplification and detection of *C. trachomatis* in duplex reactions containing the Internal Control reverse primer due to the formation of primer dimers during thermal cycling.

The decision was taken to design primers without redesign a primer to this remove the 3' homology. It was decided to re-design the *C. trachomatis* reverse primer due to the Internal Control primer sets working well in existing duplex assays using other DNA targets. The *C. trachomatis* forward primer had to be subsequently amended to the $T_m$ of the reverse primer increasing due to its added bases. The new *C. trachomatis* forward and reverse primers had the following sequences:

```
New CT fw primer:
                            (SEQ ID NO: 17)
    5'-caaacctcac tagtcagcat caagctagg-3'

New CT rv primer:
                            (SEQ ID NO: 19)
    5'-agattccaga ggcaatgcca aagaaa-3'
```

The seven additional base pairs that were added, on to the 5' end of the CT forward primer were intended to be a 5' continuation of the sequence to the strand of the *C. tracho-*

*matis* chromosomal DNA that the primer was designed for. However, an error in primer design meant that these seven additional bases were in fact complementary to what was intended for inclusion. Nevertheless, this appears to have achieved the aim of bringing the $T_m$s of each primer closer to each other, whilst retaining the performance previously observed with the "old" *C. trachomatis* forward primer (SEQ ID NO: 6).

Although these seven non-complementary bases were mistakenly added to the 5' end of the forward primer instead of seven complementary bases, experimentation proceeded with testing the new *C. trachomatis* primer set in a duplex reaction with the Internal Control DNA and fw and rv primers. Initially; primer compatibility was checked using symmetric PCR, analyzing the amplicons generated using agarose gel electrophoresis. This experiment surprisingly showed that the new *C. trachomatis* fw and rv primers gave a limit of detection of 1 IFU, equivalent to that observed in FIGS. 6a/b. When the Internal Control Primers were added to this reaction mix, the limit of detection using electrophoresis was increased slightly to 10 IFUs (in electrochemical experiments, it has been shown to detect 1 IFU); an improvement on that observed in FIGS. 7a/b. A further experiment tested the ability of the new *C. trachomatis* and Internal Control primer sets to asymmetrically amplify the two target chromosomal DNAs using a duplex reaction, followed by electrochemical detection. These data are shown in FIG. 8.

The data shown in FIG. 8 demonstrates that the modified *C. trachomatis* primer set, when combined with the existing Internal Control primer set, permits co-amplification and electrochemical detection of these targets using duplex PCR.

Example 10

Duplex Trial 2

Figure 9:
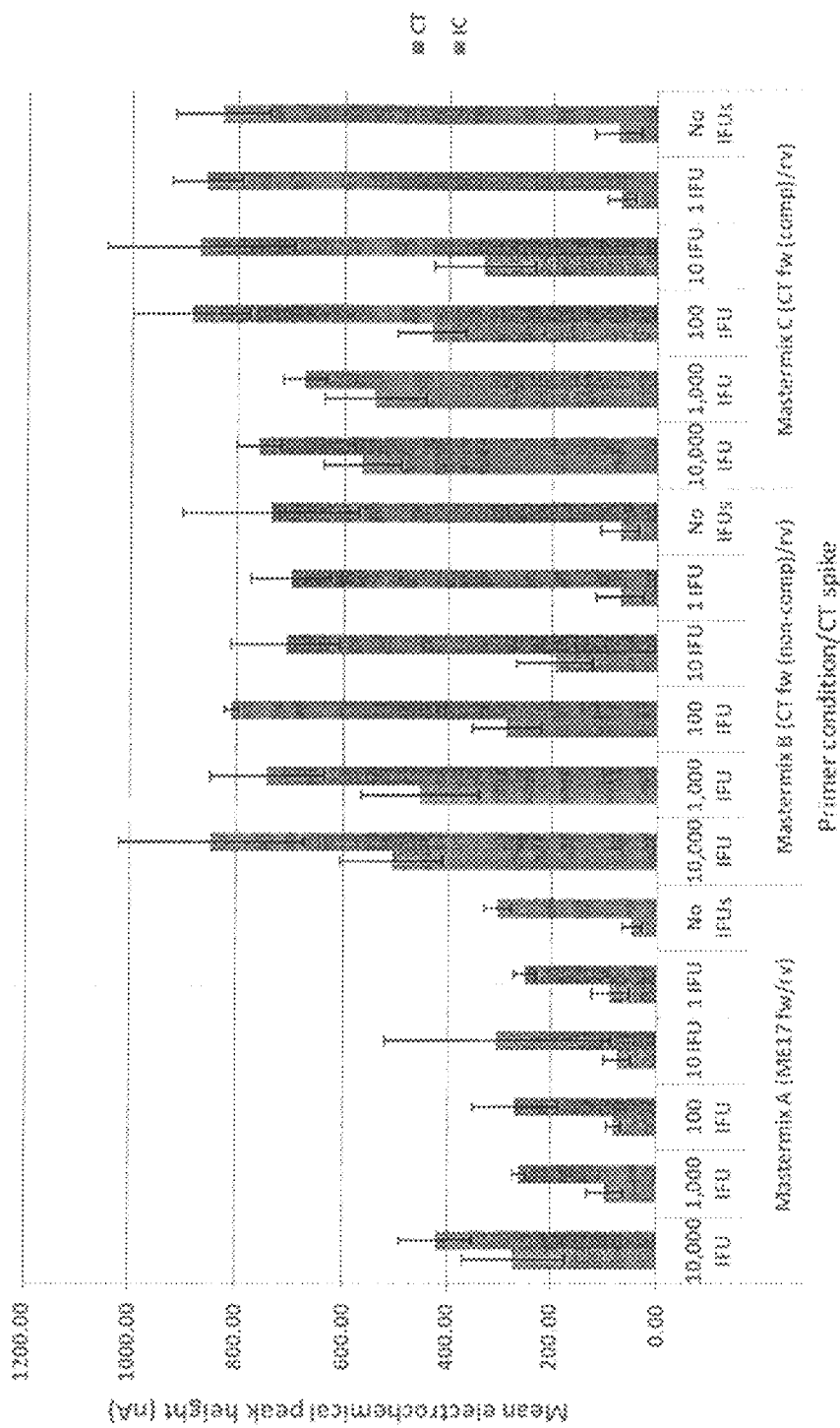

Additional experiments were carried out to assess the performance of a lengthened *C. trachomatis* forward primer which is fully complementary to the target DNA (SEQ ID NO: 18).
Results
When used in a PCR reaction with reverse primer SEQ ID NO: 19 and probe SEQ ID NO: 5 duplexed with the preferred Internal Control, the SEQ ID NO: 18 forward primer was found to function as well as the SEQ ID NO: 17 forward primer. FIG. 9 shows a comparative set of duplex experiments using 3 PCR mastermixes. "CT" indicates the value for *C. trachomatis*, "IC" indicates the value for Internal Control "IFU"=infection units.

The Internal Control reactions used primers SEQ ID NO: 11 and 12 and probe SEQ. ID NO: 14 throughout.

Mastermix A used primers SEQ ID NOS; 6 and 7 and probe SEQ ID NO: 5 for the *C. trachomatis* reaction and show a limit of detection between 10,000 and 1,000 IFU.

Mastermix B used primers SEQ ID NOS: 17 and 19 and probe SEQ ID NO: 5 for the *C. trachomatis* reactions and shows a limit of detection between 10 IFU and 1 IFU.

Mastermix C used primers SEQ ID NOS: 18 and 19 and probe SEQ ID NO: 5 for the *C. trachomatis* reactions and shows a limit of detection between 10 and 1 IFU.

The data presented in Examples 9 and 10 demonstrate that nucleic acid amplification reactions using *C. trachomatis* forward primers SEQ ID NOS: 17 and 18 and reverse primer SEQ ID NO: 19 are especially suitable for use with the internal control nucleic acid and amplification of the invention in duplex reactions. The good performance of primers having the sequence of SEQ ID NO: 17 is especially surprising given that its sequence is incompletely complementary to its target.

The invention claimed is:
1. A method of sequence-specific detection of a nucleic acid sequence from natural *Chlamydia trachomatis* chromosome in a clinical sample, the method comprising a) amplifying a target nucleic acid sequence contained within SEQ ID NO: 1 in the clinical sample to obtain a nucleic acid product consisting of a sequence contained within SEQ ID NO: 1 and/or its complement and comprising at least 15 contiguous nucleotide residues contained within SEQ ID NO: 1 and/or its complement; and b) performing sequence-specific detection of the nucleic acid product in step a) comprising a step of nucleic acid hybridization of the nucleic acid product to a nucleic acid probe to generate a detectable nucleic acid, and a step of electrochemically detecting the detectable nucleic acid, thereby detecting the nucleic acid sequence from natural *Chlamydia trachomatis* chromosome.

2. The method as claimed in claim 1, wherein the nucleic acid probe comprises a nucleic acid sequence comprising at least 15 contiguous nucleotide residues contained in SEQ ID NO: 4

```
SEQ ID NO: 4:
ccgtcctgtc cgctggttct tccttacttt ttt
``` or its complement; wherein the probe hybridizes within SEQ ID NO: 1.

3. The method as claimed in claim 1, wherein the nucleic acid probe comprises a nucleic acid sequence comprising the sequence in SEQ ID NO: 5

```
SEQ ID NO: 5:
ctgtccgctg gttcttcctt act
``` or its complement; wherein the probe hybridizes within SEQ ID NO: 1.

4. The method as claimed in claim 1 wherein the nucleic acid probe comprises at least 10 contiguous nucleotide residues contained in SEQ ID NO: 4

```
SEQ ID NO: 4:
ccgtcctgtc cgctggttct tccttacttt ttt
``` or its complement; wherein the probe hybridizes within SEQ ID NO: 1.

5. The method as claimed in claim 1, wherein said sequence specific detection follows amplification of the target nucleic acid sequence using the polymerase chain reaction, transcription mediated amplification, nucleic acid sequence based amplification (NASBA), helicase-dependent amplification, recombinase polymerase amplification, strand displacement amplification, or loop-mediated isothermal amplification.

6. The method as claimed in claim 1, wherein said amplifying is by polymerase chain reaction (PCR) and comprises the use of a forward PCR primer and a reverse PCR primer, wherein said forward PCR primer comprises a nucleic acid having the sequence given in SEQ ID NO: 18 or SEQ ID NO: 6

```
SEQ ID NO: 6:
cactagtcag catcaagcta gg;

SEQ ID NO: 18:
gtttggacac tagtcagcat caagctagg
``` and wherein said reverse PCR primer comprises a nucleic acid having the sequence given in SEQ ID NO: 19 or SEQ ID NO: 7

```
SEQ ID NO: 7:
t tccagaggc a a tgccaaag;

SEQ ID NO: 19:
agattccaga ggcaatgcca aagaaa,
``` and wherein the forward and reverse PCR primer hybridize within SEQ ID NO: 1.

7. The method as claimed in claim 6, wherein said polymerase chain reaction comprises the use of a nucleic acid probe comprising a nucleic acid sequence, said nucleic acid sequence comprising between 18 and 28 nucleic acid residues given in SEQ NO: 4

```
SEQ ID NO: 4:
ccgtcctgtc cgctggttct tccttacttt ttt
``` or its complement; wherein the probe hybridizes within SEQ ID NO: 1.

8. The method as claimed in claim 7, wherein said nucleic acid probe comprises a nucleic acid sequence given in SEQ ID NO: 5

```
SEQ ID NO: 5:
ctgtccgctg gttcttcctt act.
``` wherein the probe hybridizes within SEQ ID NO: 1.

9. The method as claimed in claim 1, further comprising a step of adding genomic DNA derived from *Pectobacterium atrosepticum* to the sample and detecting genomic DNA derived from *Pectobacterium atrosepticum* in the sample, to provide an internal positive control.

10. The method as claimed in claim 9, wherein said *Pectobacterium atrosepticum* is of the strain ATCC BAA-672.

11. The method as claimed in claim 9, further comprising performing a polymerase chain reaction using a control forward PCR primer and a control reverse PCR primer which hybridize to a target nucleic acid sequence found within the nucleic acid sequence of SEQ ID NO: 8

```
SEQ ID NO: 8:
ctaccgtgta gggtcatagg cattgacctc atggctccac ggaatcgtgc gatcgtcaac tgcgacgtgc cattcacagt gcgtaagagc accgcgaatc tcggataaac actggcacca gtgctgtacg ccaatccaga ttgcttcttc ctcgctgtcg ggaagtttgg ttgaaccgga gagcacgatc cctttcctaa agacgttacc gattttcaca ttgagggcga aatcaaagga ttcccagttc aggcctgtac ccgtcgtcag atatttctca atttggtcat taacagaatg gcgttggacg atctccttca cggcagatat ctctttctgg ctcagggatt ttttacgtcg agcggtgtaa tagagcgaaa ttgccac;
``` or its complement.

12. The method as claimed in claim 11, wherein:
a) said control forward PCR primer comprises a nucleic acid sequence comprising between 13 and 23 contiguous nucleotide residues selected from SEQ ID NO: 9;

SEQ ID NO: 9:
ctcgctgtcg ggaagtttgg ttgaaccg;

and b) said control reverse PCR primer comprises a nucleic acid sequence comprising between 15 and 25 contiguous nucleotide residues selected from SEQ ID NO: 10

SEQ ID NO: 10:
acaggcctga actgggaatc ctttgatttc;

or wherein said control forward PCR primer comprises a nucleic acid sequence that is the complement of the reverse primer as defined in part b) above and said control reverse PCR primer comprises a nucleic acid sequence that is the complement of the forward primer as defined in part a) above.

13. The method as claimed in claim 12, wherein said control forward PCR primer comprises a nucleic acid having the sequence given in SEQ ID NO: 11

SEQ ID NO: 11:
tgtcgggaag tttggttg and wherein said control reverse PCR primer comprises a nucleic acid having the sequence given in SEQ ID NO: 12

SEQ ID NO: 12:
cctgaactgg gaatcctttg.

14. the method as claimed in claim 11, wherein a) the control forward PCR primer according to claim 11 comprises a nucleic acid sequence comprising between 8 and 18 contiguous nucleotide residues selected from SEQ ID NO: 9;

SEQ ID NO: 9:
ctcgctgtcg ggaagtttgg ttgaaccg;

and b) the control reverse PCR primer according to claim 11 comprises a nucleic acid sequence comprising between 10 and 20 contiguous nucleotide residues selected from SEQ ID NO: 10, SEQ ID NO: 10:
acaggcctga actgggaatc ctttgatttc.

15. The method as claimed in claim 11, wherein a) the control forward PCR primer according to claim 11 comprises a nucleic acid sequence comprising between 8 and 18 contiguous nucleotide residues selected from SEQ ID NO: 9;

SEQ ID NO: 9:
ctcgctgtcg ggaagtttgg ttgaaccg;

and b) the control reverse PCR primer is according to claim 11.

16. The method as claimed in claim 11 wherein a) the control forward PCR primer is according to claim 11; and b) the control reverse PCR primer according to claim 11 comprises a nucleic acid sequence comprising between 10 and 20 contiguous nucleotide residues selected from SEQ ID NO: 10, SEQ ID NO: 10:
acaggcctga actgggaatc ctttgatttc.

17. The method as claimed in claim 9, wherein said polymerase chain reaction comprises the use of a control nucleic acid probe comprising a nucleic acid sequence, said nucleic acid sequence comprising between 18 and 28 nucleic acid residues given in SEQ ID NO: 13

SEQ ID NO: 13:
ggagagcacg atccctttcc taaagacgtt acc or its complement.

18. The method as claimed in claim 17, wherein said nucleic acid probe comprises a nucleic acid sequence given in SEQ ID NO: 14

SEQ ID NO: 14:
gcacgatccc tttcctaaag acg.

19. The method according to claim 9, wherein said polymerase chain reaction comprises the use of a control nucleic acid probe comprising a nucleic acid sequence, said nucleic acid sequence comprising between 13 and 23 nucleic acid residues given in SEQ ID NO: 13

SEQ ID NO: 13:
ggagagcacg atccctttcc taaagacgtt ace or its complement.

* * * * *

SEQUENCE LISTING

<160> NUMBER OF SEQ ID NOS: 21

<210> SEQ ID NO 1
<211> LENGTH: 252
<212> TYPE: DNA
<213> ORGANISM: Chlamydia trachomatis

<400> SEQUENCE: 1

```
atgaattcaa atatagaata taggcaatat cgtatagata tactgagctg ttttatctgc      60
ttgctaatga tggtttggac actagtcagc atcaagctag gagattctct aggaggcatc     120
attcctggat gcttaggata cttactggct aaaaggaagc atcgccgtcc tgtccgctgg     180
ttcttcctta cttttttctt tggcattgcc tctggaatct tccttgtcgt tcttcatcct     240
aagcaaaagt aa                                                         252
```

<210> SEQ ID NO 2
<211> LENGTH: 32
<212> TYPE: DNA
<213> ORGANISM: Artificial
<220> FEATURE:
<223> OTHER INFORMATION: PCR Primer

<400> SEQUENCE: 2

```
ttggacacta gtcagcatca agctaggaga tt                                    32
```

```
<210> SEQ ID NO 3
<211> LENGTH: 30
<212> TYPE: DNA
<213> ORGANISM: Artificial
<220> FEATURE:
<223> OTHER INFORMATION: PCR Primer

<400> SEQUENCE: 3
gaagattcca gaggcaatgc caaagaaaaa                                    30

<210> SEQ ID NO 4
<211> LENGTH: 33
<212> TYPE: DNA
<213> ORGANISM: Artificial
<220> FEATURE:
<223> OTHER INFORMATION: Detection probe

<400> SEQUENCE: 4
ccgtcctgtc cgctggttct tccttacttt ttt                                33

<210> SEQ ID NO 5
<211> LENGTH: 23
<212> TYPE: DNA
<213> ORGANISM: Artificial
<220> FEATURE:
<223> OTHER INFORMATION: Detection probe

<400> SEQUENCE: 5
ctgtccgctg gttcttcctt act                                           23

<210> SEQ ID NO 6
<211> LENGTH: 22
<212> TYPE: DNA
<213> ORGANISM: Artificial
<220> FEATURE:
<223> OTHER INFORMATION: PCR primer

<400> SEQUENCE: 6
cactagtcag catcaagcta gg                                            22

<210> SEQ ID NO 7
<211> LENGTH: 20
<212> TYPE: DNA
<213> ORGANISM: Artificial
<220> FEATURE:
<223> OTHER INFORMATION: PCR primer

<400> SEQUENCE: 7
ttccagaggc aatgccaaag                                               20

<210> SEQ ID NO 8
<211> LENGTH: 387
<212> TYPE: DNA
<213> ORGANISM: Pectobacterium atrosepticum

<400> SEQUENCE: 8
ctaccgtgta gggtcatagg cattgacctc atggctccac ggaatcgtgc gatcgtcaac    60
tgcgacgtgc cattcacagt gcgtaagagc accgcgaatc tcggataaac actggcacca   120
gtgctgtacg ccaatccaga ttgcttcttc ctcgctgtcg ggaagtttgg ttgaaccgga   180
gagcacgatc cctttcctaa agacgttacc gattttcaca ttgagggcga aatcaaagga   240
ttcccagttc aggcctgtac ccgtcgtcag atatttctca atttggtcat taacagaatg   300
gcgttggacg atctccttca cggcagatat ctctttctgg ctcagggatt ttttacgtcg   360
```
agcggtgtaa tagagcgaaa ttgccac                                                  387

<210> SEQ ID NO 9
<211> LENGTH: 28
<212> TYPE: DNA
<213> ORGANISM: Artificial
<220> FEATURE:
<223> OTHER INFORMATION: PCR primer

<400> SEQUENCE: 9
ctcgctgtcg ggaagtttgg ttgaaccg                                                 28

<210> SEQ ID NO 10
<211> LENGTH: 30
<212> TYPE: DNA
<213> ORGANISM: Artificial
<220> FEATURE:
<223> OTHER INFORMATION: PCR primer

<400> SEQUENCE: 10
acaggcctga actgggaatc ctttgatttc                                               30

<210> SEQ ID NO 11
<211> LENGTH: 18
<212> TYPE: DNA
<213> ORGANISM: Artificial
<220> FEATURE:
<223> OTHER INFORMATION: PCR Primer

<400> SEQUENCE: 11
tgtcgggaag tttggttg                                                            18

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
cctgaactgg gaatcctttg                                                          20

<210> SEQ ID NO 13
<211> LENGTH: 33
<212> TYPE: DNA
<213> ORGANISM: Artificial
<220> FEATURE:
<223> OTHER INFORMATION: Detection probe

<400> SEQUENCE: 13
ggagagcacg atccctttcc taaagacgtt acc                                           33

<210> SEQ ID NO 14
<211> LENGTH: 23
<212> TYPE: DNA
<213> ORGANISM: Artificial
<220> FEATURE:
<223> OTHER INFORMATION: Detection probe

<400> SEQUENCE: 14
gcacgatccc tttcctaaag acg                                                      23

<210> SEQ ID NO 15
<211> LENGTH: 39
<212> TYPE: DNA
<213> ORGANISM: Artificial

-continued

```
<220> FEATURE:
<223> OTHER INFORMATION: PCR primer

<400> SEQUENCE: 15
tgatgswwws swcactagtc agcatcaagc taggagatt                    39

<210> SEQ ID NO 16
<211> LENGTH: 36
<212> TYPE: DNA
<213> ORGANISM: Artificial
<220> FEATURE:
<223> OTHER INFORMATION: PCR primer

<400> SEQUENCE: 16
aaggaagatt ccagaggcaa tgccaaagaa aaaagt                       36

<210> SEQ ID NO 17
<211> LENGTH: 29
<212> TYPE: DNA
<213> ORGANISM: Artificial
<220> FEATURE:
<223> OTHER INFORMATION: PCR primer

<400> SEQUENCE: 17
caaacctcac tagtcagcat caagctagg                               29

<210> SEQ ID NO 18
<211> LENGTH: 29
<212> TYPE: DNA
<213> ORGANISM: Artificial
<220> FEATURE:
<223> OTHER INFORMATION: PCR primer

<400> SEQUENCE: 18
gtttggacac tagtcagcat caagctagg                               29

<210> SEQ ID NO 19
<211> LENGTH: 26
<212> TYPE: DNA
<213> ORGANISM: Artificial
<220> FEATURE:
<223> OTHER INFORMATION: PCR primer

<400> SEQUENCE: 19
agattccaga ggcaatgcca aagaaa                                  26

<210> SEQ ID NO 20
<211> LENGTH: 39
<212> TYPE: DNA
<213> ORGANISM: Artificial
<220> FEATURE:
<223> OTHER INFORMATION: PCR primer

<400> SEQUENCE: 20
tgatgcaaac ctcactagtc agcatcaagc taggagatt                    39

<210> SEQ ID NO 21
<211> LENGTH: 39
<212> TYPE: DNA
<213> ORGANISM: Artificial
<220> FEATURE:
<223> OTHER INFORMATION: PCR primer

<400> SEQUENCE: 21
tgatggtttg gacactagtc agcatcaagc taggagatt                    39
```